(12) United States Patent
Neftel et al.

(10) Patent No.: US 10,668,212 B2
(45) Date of Patent: Jun. 2, 2020

(54) DETECTION OF AN INFUSION ANOMALY

(71) Applicant: Debiotech S.A., Lausanne (CH)

(72) Inventors: Frédéric Neftel, Crans-Montana (CH); Christophe Conan, Lausanne (CH)

(73) Assignee: Debiotech S.A., Lausanne (CH)

( * ) Notice: Subject to any disclaimer, the term of this patent is extended or adjusted under 35 U.S.C. 154(b) by 373 days.

(21) Appl. No.: 15/505,936

(22) PCT Filed: Aug. 26, 2015

(86) PCT No.: PCT/IB2015/056468
§ 371 (c)(1),
(2) Date: Feb. 23, 2017

(87) PCT Pub. No.: WO2016/030836
PCT Pub. Date: Mar. 3, 2016

(65) Prior Publication Data
US 2018/0214634 A1    Aug. 2, 2018

(30) Foreign Application Priority Data

Aug. 26, 2014 (WO) .................. PCT/IB2014/064068
Nov. 7, 2014 (EP) ..................................... 14192383

(51) Int. Cl.
*A61M 5/168* (2006.01)
*A61M 5/142* (2006.01)
*A61F 5/443* (2006.01)

(52) U.S. Cl.
CPC .... *A61M 5/16854* (2013.01); *A61M 5/14224* (2013.01); *A61M 5/16877* (2013.01); *A61F 5/443* (2013.01); *A61M 2005/16863* (2013.01); *A61M 2005/16868* (2013.01); *A61M 2205/0294* (2013.01); *A61M 2205/18* (2013.01); *A61M 2205/502* (2013.01)

(58) Field of Classification Search
CPC .... A61M 5/16854; A61M 2005/16863; A61M 2005/16868; A61M 2205/0294; A61M 2205/18; A61M 2205/502; A61M 5/14224; A61M 5/16877; A61F 5/443
See application file for complete search history.

(56) References Cited

U.S. PATENT DOCUMENTS 5,389,078 A * 2/1995 Zalesky ............ A61M 5/14526
604/151
5,795,327 A    8/1998 Wilson et al.
(Continued)

FOREIGN PATENT DOCUMENTS

EP         1762263 A1    3/2007
WO    WO-9826818 A1 *  6/1998 ............ A61M 5/007
(Continued)

OTHER PUBLICATIONS

International Search Report for PCT/IB2015/056468, dated Nov. 16, 2015.
(Continued)

*Primary Examiner* — Brandy S Lee
(74) *Attorney, Agent, or Firm* — Andre Roland S.A.; Nikolaus Schibli

(57) ABSTRACT

The present invention relates to medical pumping devices and more precisely to the detection of dysfunctions in such devices.

20 Claims, 17 Drawing Sheets

(56) References Cited

U.S. PATENT DOCUMENTS

| | | | | |
|---|---|---|---|---|
| 6,362,591 | B1* | 3/2002 | Moberg | A61M 5/162 318/685 |
| 6,555,986 | B2* | 4/2003 | Moberg | A61M 5/162 318/685 |
| 6,716,193 | B1* | 4/2004 | Neftel | A61M 5/007 604/118 |
| 7,104,763 | B2* | 9/2006 | Bouton | A61M 5/14224 417/26 |
| 9,943,644 | B2* | 4/2018 | Hayter | A61B 5/14532 |
| 2007/0088267 | A1* | 4/2007 | Shekalim | A61M 5/145 604/134 |
| 2011/0054397 | A1* | 3/2011 | Menot | A61M 5/14224 604/110 |
| 2011/0142688 | A1* | 6/2011 | Chappel | A61M 5/16854 417/213 |
| 2011/0144585 | A1* | 6/2011 | Bianchi | A61M 5/14244 604/122 |
| 2013/0141438 | A1* | 6/2013 | Neftel | G06T 11/206 345/440 |
| 2014/0147246 | A1* | 5/2014 | Chappel | A61M 5/14244 415/1 |

FOREIGN PATENT DOCUMENTS

| | | |
|---|---|---|
| WO | WO0190577 A1 | 11/2001 |
| WO | WO2007113708 A1 | 10/2007 |
| WO | WO2007141786 A1 | 12/2007 |
| WO | WO2010023567 A1 | 3/2010 |
| WO | WO2010046728 A1 | 4/2010 |
| WO | WO2011070468 A1 | 6/2011 |
| WO | WO2012085814 A2 | 6/2012 |
| WO | WO2012176171 A1 | 12/2012 |
| WO | WO2013018011 A2 | 2/2013 |
| WO | WO2014009876 A2 | 1/2014 |
| WO | WO2014136090 A1 | 9/2014 |

OTHER PUBLICATIONS

Written Opinion of the International Searching Authority for PCT/IB2015/056468, dated Nov. 16, 2015.
Australian application n° 2015308144 Examination report dated Jun. 14, 2019.

* cited by examiner

DETECTION OF AN INFUSION ANOMALY

CROSS REFERENCE TO RELATED APPLICATIONS

The present application is a U.S. national stage application of PCT/IB2015/056468 filed on Aug. 26, 2015 designating the United States, and claims foreign priority to European Patent Application EP 14192383.9 filed on Nov. 7, 2014, and also claims foreign priority to the International patent application PCT/IB2014/064068 filed on Aug. 26, 2014, the contents of all three documents being herewith incorporated by reference in their entirety.

FIELD OF INVENTION

The present invention relates to infusion systems and more precisely to the detection of dysfunctions in the performance or efficiency of such systems.

State of the Art

The detection of an anomaly (for example: dysfunctions in performance or efficiency), especially in medical devices, is important because the life of the patient may depend on proper functioning and/or efficiency of said devices. For instance, the potentially dangerous results of a failure are typically over-infusion, under-infusion or uncontrolled infusion of a fluid to a patient. Examples of dysfunctions are leaks, occlusions or presence of air bubbles in the pumping line. State-of-the-art devices and methods for detecting dysfunctions in medical devices are for instance disclosed in the following documents: U.S. Pat. No. 6,555,986 B2, EP 1 762 263 A1 and U.S. Pat. No. 7,104,763 B2, the entire disclosure of which is incorporated herein by reference.

When using certain fluids such as drugs, and in particular insulin, the detection of an anomaly (for example occlusion) may be of particular importance. For example, it is known that catheters or infusion line may be occluded (totally or partially) in numerous circumstances, or that the diffusion of the fluid in the tissue (such as for example in the sub-cutaneous region, in the dermis or in the muscle) may be limited or restricted. Any such undetected anomaly (herein: total or partial occlusion or diffusion limitation or restriction) may result in under-delivery or inaccurate delivery of the fluid especially if it remains undetected for a long period of time. One of known drawbacks of state of the art devices is that the anomaly is detected too late (for example: the apparatus of the syringe-pump tend to detect too late a full occlusion and cannot detect a partial occlusion) or the patient is alerted too quickly and too often (thus the patient no longer considers the alerts).

Ideally, the medical devices must be adapted to detect all anomalies of the devices which are described by the following documents: US 2011/0142688 A1 and US 2014/0147246 A1, these documents are fully incorporated to the present document by reference.

However, for economic reasons, the devices have a limited number of sensors and sometimes only one sensor is used to detect several distinct anomalies. Nevertheless, sometimes the device misinterprets the signal of the sensor or the anomaly and the device gives a wrong alert to the patient. For example, some devices comprise a zinc-air battery which needs air to operate. Thus a vent is necessary in the housing of the device. If this vent is clogged then the battery will be depleted very rapidly and the state-of-the-art devices may conclude to a low battery level while the real anomaly is that the vent is clogged . . . . Thus, changing the battery will not resolve the root cause of the problem. To detect the real failure mode and therefore to limit the triggering of false alarm, the medical device shall process the anomaly in a smart way.

In addition of the previous drawbacks, the state-of-the-art devices only alert the patients but the patients cannot solve (or do not know how to solve) the anomaly. For example when an occlusion occurs, the medical device alerts the patient but this information is not sufficiently relevant. The occlusion may be partial, may release over time, may be located in the pump or in the infusion set or in the tissue of the patient. With the state-of-the-art devices, the patient does not have relevant information so as to solve the problem.

Thus, in addition to detecting several anomalies, an ideal medical device should alert the patient only if necessary and should try to solve alone the detected anomaly. Preferentially, the future medical devices should improve the treatment compliance as well as the life and security of the patient.

GENERAL DESCRIPTION OF THE INVENTION

In order to correct the drawbacks cited above, the present document discloses a smart medical system which is an infusion system. Said infusion system has been developed to accurately deliver a solution to a patient and to detect and correctly interpret any anomaly that could alter the device functionality.

Said infusion system comprises a container adapted to store a solution, an infusion set adapted to infuse the solution into or on the body of a patient, a pumping unit adapted to move the solution from the container to the infusion set, and at least one sensor. The infusion system further comprises a fluidic pathway in which the solution flows from the container to the infusion set and a processor configured to communicate with the sensor and the pumping unit. The solution is a fluid which may be a liquid for example a drug. In one embodiment, said system is adapted to use with insulin for patient with type 1 and type 2 diabetes mellitus; as described by the following documents: WO 2007/113708, WO 2010/023567, WO 2012/176171 and WO 2014/009876. The entire disclosure of these documents is incorporated herein by reference.

The infusion set comprises a cannula or a micro-needle adapted to infuse the solution into a dedicated infusion site. Said cannula or micro needle is in fluid communication with the reservoir. In this document, the terms "infusion site" must be understood as the location where the fluid is injected or infused. It may be a specific location in/on the skin of the patient, for example in the sub-cutaneous region, in the dermis, in the muscle or in a vein.

In one embodiment, the reservoir is a cartridge in which the drug is pushed by a piston forming the pumping unit. In other and preferred embodiment, the pumping unit may comprise a membrane pump for example a MEMS micro pump which allows accurate delivery and failure detection capabilities. Such device is particularly adapted to detect several anomalies because this device does not comprise deformable elements like the tube or any other flexible element in the fluidic pathway. Such device is described in the following documents: WO 2001/90577, WO 2014/136090 and WO 2010/046728. The entire disclosure of these documents is incorporated herein by reference.

In one embodiment, the pump is actuated by a pump actuator which may be a piezo electric ceramic controlled by a processor as described in the following documents: WO 2011/070468, WO 2012/085814 and WO 2013/018011. The entire disclosure of these documents is incorporated herein by reference.

A first aspect of the invention provides a medical system configured to process signal in a smart way so as to identify a dysfunction of the medical system, to identify a status of an element of the system and/or to quantify the amount of fluid actually infused or the amount of the fluid which should have been infused. To reach one of these purposes, the pumping unit may comprise a pressure sensor which measures a pressure of the solution in the fluidic pathway. This pressure sensor may be a differential or gauge pressure sensor, indicating the difference of pressure between the solution and an exterior pressure (which could be, for example, outside of the fluidic pathway inside or outside the housing of the medical system). The pressure sensor is preferentially located "in-line", that is to say in the fluidic pathway for example in the reservoir, in the pumping chamber, in downstream or upstream of the pumping chamber or near the infusion site (for example in the infusion set). Preferentially, the pressure sensor is located in the pumping chamber or downstream of the pumping chamber (for example after an outlet valve) so as to directly measures the fluid pressure. The system may comprise other sensor, for example a sensor (such as a Hall Effect sensor) adapted to detect if the pumping unit is correctly connected to the infusion set, immersion sensor, temperature sensor, accelerometer or flowmeter.

According to an embodiment the medical device is adapted to monitor the signal sent by a sensor. Preferentially, the processor is coupled to the sensor and/or to the pumping actuator. Said processor is configured to analyze and to rationally interpret the data so as to discriminate different potential events. The sensor sends a signal to the processor which processes the signal. Preferentially, at each stroke of the pump, the processor may analyze the pressure profile, the actuation profile and/or the position profile of the actuator. The processor analyses the pressure profile measured by this sensor during the stroke. The processor selects at least two data of at least one profile in order to determine the type of events which occurs. In particular, the processor may analyze the fluid pressure at a predetermined time, depending on the actuation profile. For example, the processor determines a first pressure and upon a time period, determines a second pressure during the same stroke or after the stroke. The processor may also be adapted to compute the slope of the pressure profile. In one embodiment, the infusion system comprises two distinct pressure sensors located at two distinct locations along the fluidic pathway. Each pressure sensor experiences a specific pressure profile depending on its specific location along the fluidic pathway; both pressure signals, which could be for analogic or digital signals, may be processed by the processor. For instance, the FIG. 2 shows several pressure profiles measured by a sensor located into the pumping chamber (i.e. between the inlet and the outlet valves) during a stroke and the FIG. 3 shows several pressure profiles measured by a sensor located downstream of the outlet valve during said stroke. A memory may store all or part of the data and the processor may compute at least a rate of decrease, a median and at least a mean of said data. The processor may also compare or combine the data obtained by the two different sensors.

For example, the processor may be configured to detect and distinguish several operating anomalies which may be:
An overpressure located upstream the pumping chamber (for example overpressure in the reservoir, . . . ),
Leak of one or the two valves, of the pumping chamber, or any part of the fluidic pathway,
Total occlusion,
Partial occlusion,
An overpressure located downstream the pumping chamber (for example due to an occlusion, . . . ),
Air bubble in the Pump chamber or any part of the fluidic pathway,
Under-pressure due to lack of insulin (for example when the reservoir is almost empty),
Other conditions leading to possible under-, mis-, or over-delivery (particles in the Pumping chamber, incomplete stroke, glass cap leakage)

In one embodiment, the processor and the sensor are adapted to detect and discern a partial occlusion from a total occlusion which occurs downstream of the pumping unit. In this document, the term "an occlusion" must be understood as any event which results to a partial or full clogging (blockage or obstruction) of the fluidic pathway and therefore (partially or totally) prevents the system to infuse the solution toward the infusion site. In particular, the clogging (blockage or obstruction) may be mechanical (a particle in the fluidic pathway, . . . ). During a full occlusion, the infusion system cannot infuse at all the solution to the patient. The pressure sensor detects a quick growth of the solution pressure into the fluidic pathway (for example during actuation). A partial occlusion is more difficult to detect and to characterize. But thanks to an embodiment of our system, the total and partial occlusion can be quickly detected and the amount of infused, or non-infused, fluid may be estimated by the processor. In said embodiment, only one pressure sensor may be used, said sensor being preferentially located downstream of the pumping unit, for example downstream of the outlet valve. In particular, to distinguish partial from total occlusion, the processor analyses the fluid pressure at a predetermined time, which could be related to the piezo actuation sequence or directly to the pressure profile itself. For instance the time at which occurs a peak or a minimum or maximum value in the pressure profile may be used as a time reference for the pressure profile analysis by the processor. The major difference between partial and total occlusion relies on different relaxation pressures after stroke (or the positive peak of pressure during the infusion cycle) and the occlusion can be evaluated or estimated or detected thanks to the analysis of the slope of the pressure profile (i.e. the pressure variation profile) after the pressure peak.

In one embodiment, when a partial occlusion is detected, the processor changes the actuation profile of the actuator, for example, the pumping membrane, which travels from a bottom to a top position during infusion phase (or PUSH phase), is maintained at its top position during a longer duration or until the pressure in the fluid reaches a predetermined threshold pressure. This operating mode is described below in this document.

In one embodiment, the system comprises a screen (for example a touchscreen of a remote controller adapted to control the pumping device) adapted to alert or inform the patient of the fault conditions or events. Said screen may be used to prompt the patient to take action in such a way that the patient can stop the cause of the problem before the anomaly becomes too much important. This operating mode is described below in this document.

According to one embodiment, the medical device is adapted to check a first interpretation (or assumption) so as to confirm the anomaly and prevents disturbing the patient, before to alert the patient. In this case, the pumping device is adapted to command another stroke (for example in addition to the recommended treatment), to change the type of actuation (actuation profile) or to use another data to check the information. Thus, the processor of the device may use a decision tree to determine the real anomaly. For example, if the pumping device detects an overpressure by a pressure sensor, this overpressure may be caused by an overpressure in the reservoir or by an occlusion located downstream of the outlet valve. Thus the system may generate at least one other stroke or use a second pressure sensor so as to allow defining the real cause of the overpressure. In other terms, the system is adapted to detect an anomaly and command a specific action (depending on the data sent to the processor) so as to deduct or confirm the type of anomaly.

According to one embodiment, the medical device is adapted to monitor and record the anomalies so as to solve a redundant problem. For example, the pumping device may comprise a battery which needs oxygen to operate (e.g. ZnAir type battery). This battery may be located in a space which is vented (for instance, in an electronic part of the pumping device). If the vent is clogged, the battery will consume the residual oxygen trapped in this space, and when the residual oxygen is consumed, the battery will stop delivering power. An indication device may alert or inform the patient to change the battery, whereas the problem is not the battery but the vent. The system may comprise a memory which stores the events and if the next battery fails too quickly, the processor concludes that the vent is probably clogged. The processor can for instance monitor a typical characteristic of the battery (usually its voltage) and alarm the patient that the vent is clogged if the battery voltage falls down from its nominal to a threshold value in less than a predetermined duration that is a function of the dead volume of the compartment surrounding the battery (or in other words the total volume of air surrounding the battery compartment when clogged). Thus the device may prompt the patient to check the vent, to clean it according to the user manual procedure or to change the housing comprising the vent. Thus, the system stores the events and depending on at least one previous event, the system may deduct the real event or the cause of the event(s). In this case, the processor may use a decision tree.

According to another embodiment, the medical device is adapted to monitor the effective amount of fluid which has been delivered. The medical device comprises an in-line pressure sensor and a fluidic pathway (whose characteristics are known). A processor is electronically coupled to the sensor so as to directly receive the signal from the sensor. The processor is configured to analyze the signal profile and to estimate the flow rate or the amount of fluid which has been delivered. The medical device further comprises a memory in communication with the processor adapted to record the infusion data. Thanks to this embodiment, the device is adapted to estimate the fluid amount delivered and to compare this data to the amount recommended by the treatment. This information may be useful to improve the treatment or to monitor the good patient compliance. Furthermore, when an anomaly occurs (for example an occlusion), the medical device can estimate the fluid amount that should have been infused. A screen may inform the patient. Thus if the fluid is insulin, the device can prompt a remedial bolus which takes into account the amount of non-infused insulin. This latter quantity may be equal to the difference between the programmed volume and the estimation of the total volume really infused during the occlusion.

A second aspect of the invention provides a medical system configured to change of operating mode so as to switch in a specific operating mode or to solve the anomaly.

In one embodiment, the medical system comprises a safe state mode (also called suspended mode). Said suspended mode may be automatically enabled by the processor when a specific event occurs. When it occurs, an optional indication device (for example a screen) may alert the patient about the status of the pumping device. For example, if the processor detects an occlusion, the processor switches the operating mode in suspended mode so as to avoid a potential damage on the pumping unit and the indication device may prompt to change the infusion set or to apply a pressure on or to massage the infusion site (this feature is explained below in this documents).

When the anomaly or event is released, the system may be adapted to leave the suspended mode and resume therapy. Preferentially, the system computes the amount of fluid it was supposed to deliver during in the suspended mode and will compensate for it by increasing its infusion rate when leaving the suspended mode. This compensation may be partial or total. It may be done rapidly or over a predefined period of time.

In one embodiment, the infusion system comprises a pumping device removably attached to an infusion set. A sensor (as a Hall Effect sensor) may be used to detect when the pumping unit is connected or attached to the infusion set. When the sensor detects that the pumping device is disconnected from the infusion set, the suspended mode may be automatically enabled and the system computes the amount which would be infused. For example for each time period without infusion, the processor adds an amount (which represents a non-delivered volume of drug) in a counter, or at the end of the suspended mode, the processor computes the non-delivered amount. When the pumping device is reconnected, the system may suggest to the patient to completely or partially infuse the amount which has not been infused.

In one embodiment, the medical system can automatically change the actuation profile when an anomaly is detected so as to solve the problem. For example, when a partial occlusion occurs, the processor may maintain during a time period the actuator in a push position.

A third aspect of the invention provides a medical system configured to send relevant information to the patient.

According to an embodiment the medical system is adapted to inform the patient about a status of an element of the medical system. The fluidic resistance in the fluidic pathway or at the infusion site can change over time (for example, an inflammation or a nodule developed near the infusion site). The characteristic of the infusion set may also change over time (or may be defective) which causes a growth of fluidic resistance (for example, permeability of the cannula, insulin fibrils in the cannula or a kinking of the cannula).

Since the processing data allows estimating or computing a flow rate and/or a real amount infused and/or an interstitial pressure, the system can provide more information to the patient, for example:

The status of the infusion set, or
The characteristic of the infusion site, or
Other information.

By "characteristic of the infusion site", it is meant the absorption capability of the tissue (i.e. the capacity of a tissue to absorb an infused drug) or more generally the fluidic resistance in the tissue where the infusion set injects the fluid. Said characteristic of the infusion site may be different depending on the location of the infusion set on the body or in the tissue and/or can change over time. For example, if the infusion set injects the fluid near a bone or in a contracted muscle, it will be more difficult to inject and/or absorb the fluid injected than in a fat tissue, or in a released muscle. Other example, a nodule may develop near the infusion site or an inflammation near the infusion site may occur which may transiently reduce the absorption capacity of the tissue.

According to one embodiment, the medical device is adapted to prompt the patient to execute a specific action so to improve the delivery and/or solve an anomaly. In this case, the medical system comprises an indication device which displays such information to the caregivers or to the patient. Said indication device may be used for suggesting to:

Change the infusion site,
Change the cannula,
Prompt a certain behavior (e.g. movement of the patient, massage of, press against or pulling of the infusion site . . . ) in order, e.g. to release the stress on the tissue or the constraints on the cannula.

In other terms, the indication device helps the patient with his infusion site management.

A fourth aspect of the invention provides a medical system which may comprise a buffer. In one embodiment, the system may comprise all or part of the features of the system disclosed by the previous aspect of the invention. According to this aspect of invention, a buffer compartment is arranged between the pumping unit and the infusion site (or cannula). Said buffer compartment is capable of retaining a certain amount of the drug to be infused while increasing the pressure applied on the infusion site (e.g. an elastic or elastomeric bladder or any elastic or elastomeric membrane, elastic or elastomeric tubing or reservoir). Thanks to the buffer compartment, in case of an occlusion, the pressure can be maintained until the occlusion is released. Alternatively, the pressure can also be maintained in case of a partial occlusion, so that the volume to be delivered can be actually delivered in a certain period of time, which is depending on the importance of such restriction.

LIST OF FIGURES

The present invention will be better understood at the light of the following detailed description which contains non-limiting examples illustrated by the following figures:

FIGS. 1a, 1b, 1c, 1d and 1e show different elements of the delivery system.

FIG. 2 illustrates the inner detector signal during actuation as a function of the effective stroke volume FIG. 3 illustrates the outer detector signal FIG. 4 illustrates the outer detector signals in bolus mode in different conditions of partial occlusion. The blue curve (curve with triangle) is the reference signal without fluidic restriction while the red curve (curve with ring) and green curve (curve with square) have been recorded after the insertion of narrow tubing of 10 cm and 20 cm respectively.

LIST OF ELEMENT

Figure 1A:
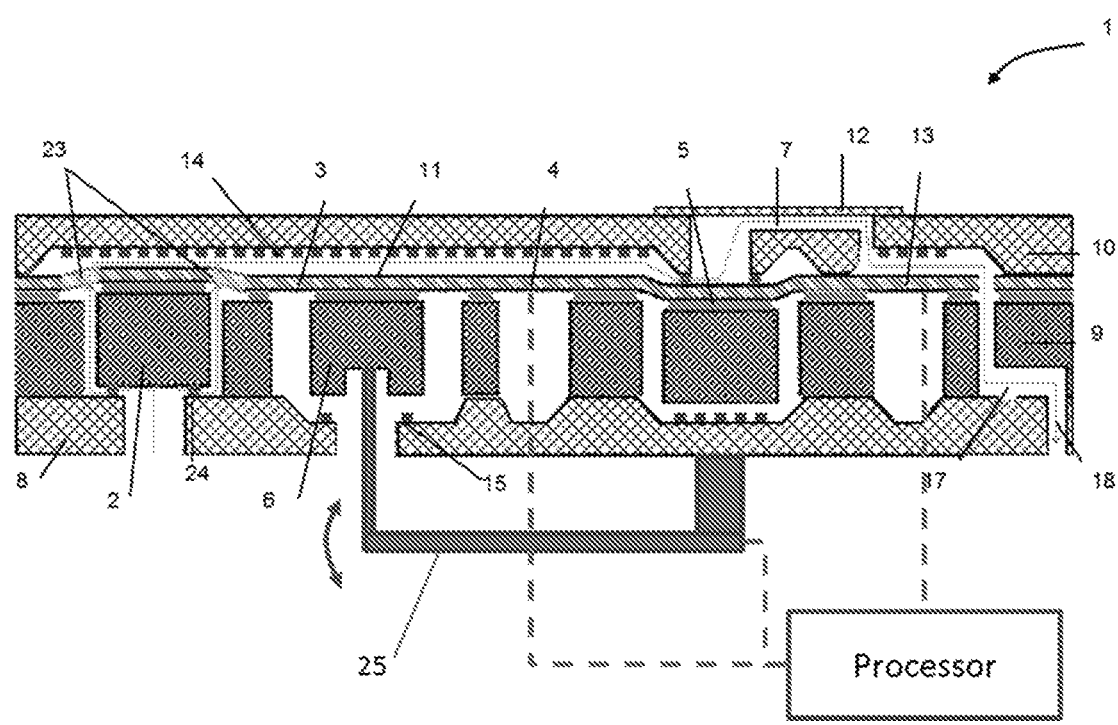

1 Pump
2 Inlet valve
3 Pumping membrane
4 Sensor membrane
5 Outlet valve
6 Mesa
7, 17 Channel
8 Base plate
9 Second plate
10 Top plate
11 Pumping chamber
12 Cover
13 Sensor membrane
14, 15, 24 anti-bonding layers
18 Outlet
23 Arm of the valve
25 Actuator
100 Pumping device
101 Disposable part
102 Non-disposable part
103 Reservoir
104 Housing
105 Vent
106 Electronic elements
107 Housing
108 Vent
109 Battery
110 Patch
111 Infusion set
112 Housing
113 Inlet port of the infusion set
114 Outlet port of the pumping device
115 Cannula
200 Remote controller
201 Screen
202 Button
203 Telecommunication device

DETAILED DESCRIPTION OF THE INVENTION

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, any direction referred to herein, such as "top", "bottom", "left", "right", "upper", "lower", and other directions or orientations are described herein for clarity in reference to the figures and are not intended to be limiting of an actual device or system. Devices and systems described herein may be used in a number of directions and orientations.

As used herein, "have", "having", "include", "including", "comprise", "comprising" or the like are used in their open ended sense, and generally mean "including, but not limited to.

As used in this specification and the appended claims, the term "or" is generally employed in its sense including "and/or" unless the content clearly dictates otherwise.

The term "substantially" as used herein, is a broad term and is used in its ordinary sense, including, without limitation, being largely but not necessarily wholly that which is specified.

The term "microprocessor" and "processor" as used herein, is a broad term and is used in its ordinary sense, including, without limitation, a computer system or processor designed to perform arithmetic and logic operations using logic circuitry that responds to and processes the basic instructions that drive a computer.

The term "ROM," as used herein, is a broad term and is used in its ordinary sense, including, but not limited to, read-only memory, which is a type of data storage device manufactured with fixed contents. ROM is broad enough to include EEPROM, for example, which is electrically erasable programmable read-only memory (ROM).

The term "RAM," as used herein, is a broad term and is used in its ordinary sense, including, but not limited to, a data storage device for which the order of access to different locations does not affect the speed of access. RAM is broad enough to include SRAM, for example, which is static random access memory that retains data bits in its memory as long as power is being supplied.

The term "RF transceiver," as used herein, is a broad term and is used in its ordinary sense, including, but not limited to, a radio frequency transmitter and/or receiver for transmitting and/or receiving signals.

The terms "connected" and "operably linked," as used herein, are broad terms and are used in their ordinary sense, including, but not limited to, one or more components being linked to another component(s) in a manner that allows transmission of signals between the components.

The term "algorithm," as used herein, is a broad term and is used in its ordinary sense, including, but not limited to, the computational processes (for example, programs) involved in transforming information from one state to another, for example using computer processing.

The term "alarm," as used herein, is a broad term and is used in its ordinary sense, including, but not limited to, audible, visual, or tactile signal that are triggered in response to detection of an anomaly.

The term "computer," as used herein, is broad term and is used in its ordinary sense, including, but not limited to, machine that can be programmed to manipulate data.

Example of Pumping Device

Figure 1B:
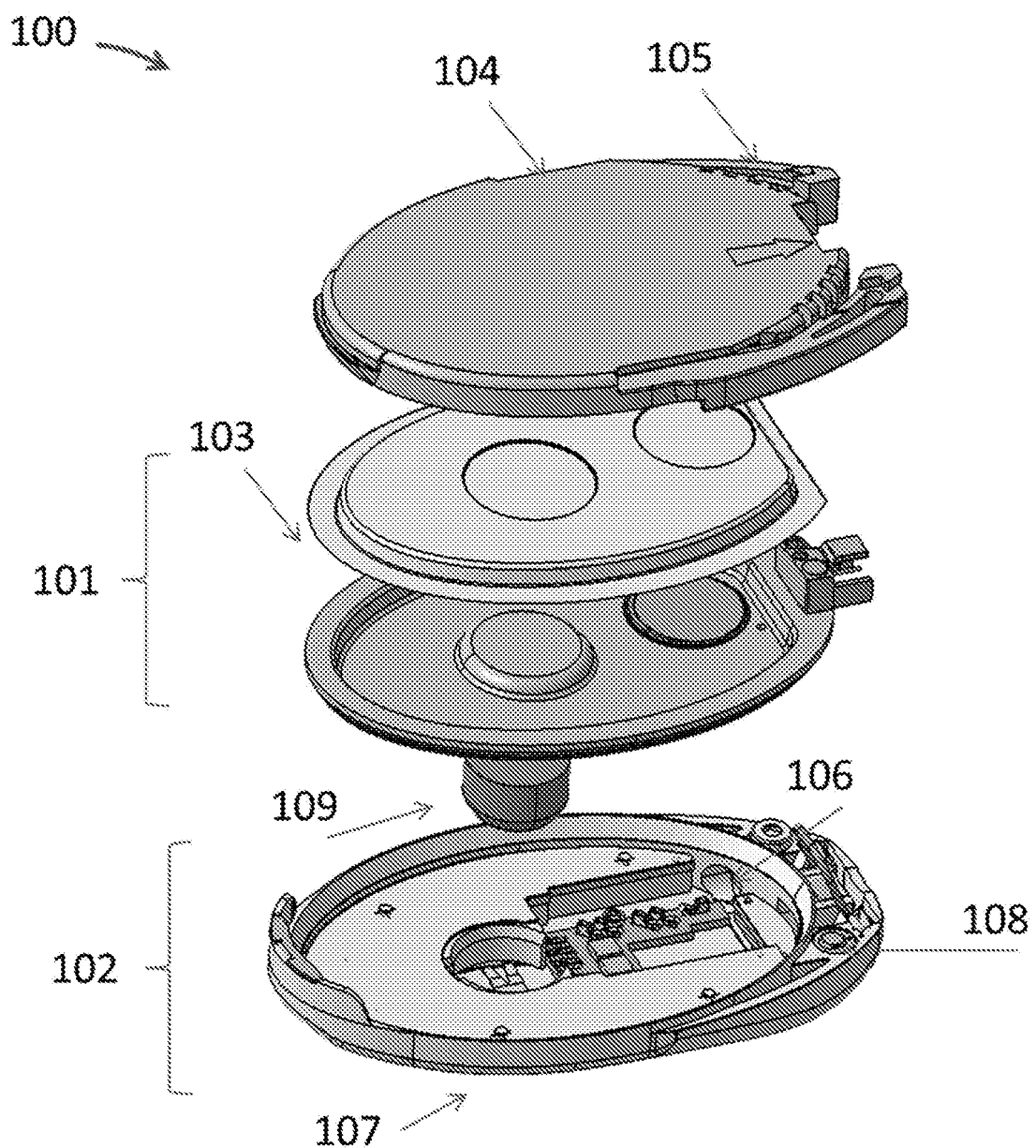

The FIG. 1b shows a pumping device 100 comprises two distinct parts. A first part is called disposable part (101) and comprises all elements which may be discarded after a predetermined duration. Said disposable part may be not re-usable after use (single use). A second part is called non-disposable part (102) and is re-usable with different (i.e. successive) disposable parts. The disposable part (101) is removably attached to the non-disposable part (102) and both form the pumping device. Both have to be attached, preferentially in a tight manner, so that the pumping device (100) works.

The disposable part comprises a reservoir (103) storing the solution. Said reservoir is arranged into a first cavity closed by a housing (104) which may comprise vent (105) for pressure equilibration (of the cavity with the exterior of the housing). The reservoir comprises an outlet which is in fluid connection with the inlet of the pumping unit. The non-disposable part (102) comprises the electronic elements (106) (for example a processor and/or a memory) which are arranged into a second cavity closed by a housing (107) which may comprise a vent (108) for ventilation of the second cavity. A battery (109) is used by the pumping device and may need air to operate (for example Zinc-air battery). Preferentially, the housing of the disposable part and the housing of the non-disposable part form at least a part of the housing (112) of the pumping device (100).

The pumping unit (not show) or the battery (109) may be arranged into the second cavity. The pumping unit or the battery (109) may be secured against the disposable part.

Example of Pumping Unit

Preferentially, the pumping unit is a "push-pull" device which comprises a pumping chamber (11) designed in such a way to pull the fluid from the reservoir (103) (to the pumping chamber (11)) and push it (from the pumping chamber (11)) to the patient. Furthermore, said pumping unit may comprise:

A pump actuator (25) adapted to change the volume of the pumping chamber. Said pump actuator may be coupled to the processor in such a way that the processor controls the pump actuator and/or monitors the position of said pump actuator (via for example a sensor). The processor may also deduct the position of the actuator depending on the actuation data.

An inlet with an optional inlet valve (2) and an outlet with an optional outlet valve (5). Said valves may be check valves. The filling of the pumping chamber is associated with negative relative pressure in the pumping chamber that opens the inlet valve and maintains closed the outlet valve (Pull of pumping membrane), while the infusion corresponds to positive relative pressure in the pumping chamber that opens the outlet valve and maintains closed the inlet valve (Push of the pumping membrane). The inlet of the pumping unit is preferably in fluid connection with an outlet of the reservoir (103) and a filter may be arranged between the reservoir and the pumping unit.

A pumping membrane (3) (which may be at least partially flexible) adapted to move between at least two positions, preferentially against mechanical stops. Every time the membrane is pulled to fill the pumping chamber, the membrane will come in contact with a mechanical structure that will stop its course (for example against the anti-bonding layers (15)). Every time the said membrane is pushed to empty the pumping chamber, it will come in contact with a mechanical stop that will again stop its course (for example against the anti-bonding layers (14)). Thanks to these mechanical stops, if for example their distance is known and constant, the pumped volume is known with a high accuracy. The system may be adapted to hold a given pumping membrane position, for example against a mechanical stop during a predetermined period of time.

In one embodiment, the delivery system comprises a pumping unit as shown in the FIG. 1*a*, which may be a reciprocating displacement MEMS. Said figure illustrates a cross section of a micro pump with the stack of a glass layer as base plate (8), a silicon layer as second plate (9), secured to the base plate (8), and a second glass layer (10) as a top plate, secured to the silicon plate 9, thereby defining a pumping chamber (11) having a volume. An actuator (25) linked to the mesa (6) allows the controlled displacement of the pumping membrane (3). A channel (7) is also present in order to connect the outlet control member, the outlet valve (5) to the outer detector not represented here and finally to the outlet port (18) placed on the opposite side of the pump.

The FIG. 1*a* further illustrates an optional cover (12) onto the channel (7), an outer detector (13), a fluidic channel (17) located downstream of the outlet valve and the outlet port (18). The pressure inside the pumping chamber varies during a pumping cycle depending on numerous factors, such as the actuation rate, the pressure at the inlet and the outlet, the potential presence of a bubble inside of the chamber, the valve characteristics and their leak rates.

The MEMS technology is suitable for the implementation of an integrated piezoresistive gauge pressure sensor (4, 13) in the silicon chip. Thanks to the very large piezoresistance factor of silicon, these sensors exhibit outstanding sensitivities, low dead volume, no hysteresis, small offset when using the so called Wheatstone bridge configuration and good linearity, the single drawback being a temperature dependence of the signal.

A first membrane (4) with strain gauges in Wheatstone bridge configuration may be placed in the pumping chamber to monitor the good functioning of the pump while another sensor (13) may be placed downstream of the outlet valve for occlusion detection purpose.

The characteristics of these gauge pressure sensors, the implantation profiles as well as the location of the resistors have been optimized to get a detector with an offset of about few hundredths of uV/V/bar and typical sensitivity from 10 to 50 of mV/V/bar in the range −1 to +1.5 bar, with a minimum resolution of 1 mbar or less. After taking into account the different errors related to mask alignments, implantation, membrane etching, position of the resistors with respect to the membrane and the crystallographic axis, the detector signal variability has been estimated at +/−7.6% at 20° C.

Other Optional Features of Delivery System

Figure 1C:
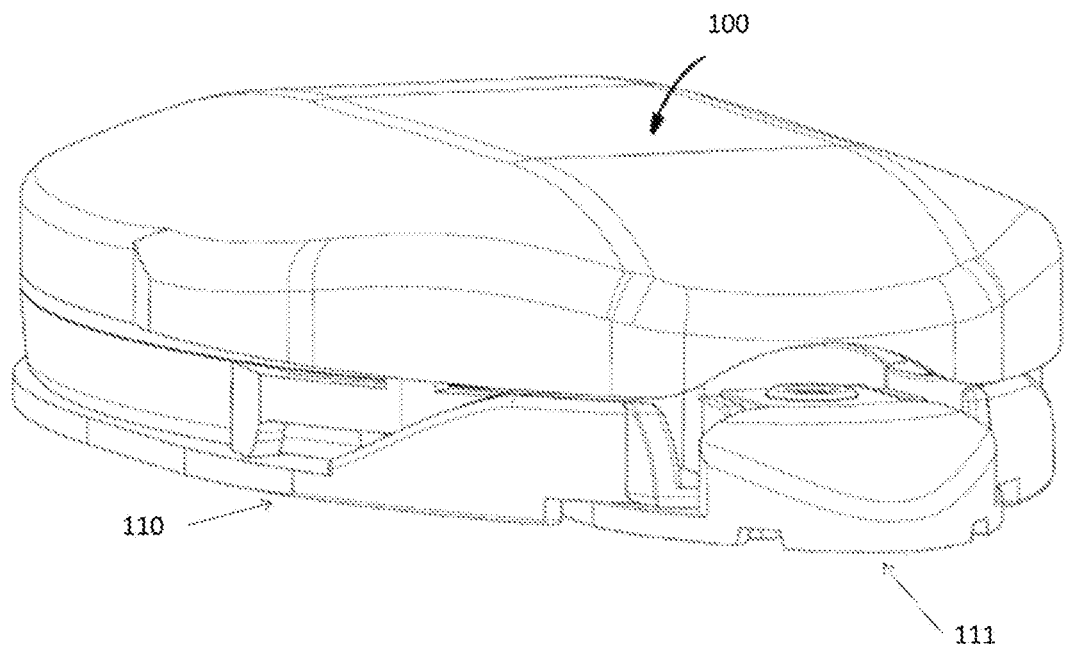

The FIG. 1*c* shows the pumping device (100) of the delivery system (also called medical system). The pumping device may be designed in such a manner as to be worn directly on a patient's skin. In this embodiment, the delivery system comprises a patch (110) adapted to be secured (via adhesive) against the skin of the patient. The patch comprises attachment elements so as to removably secure the pumping device to the patch. The system further comprises an infusion set (111) which is removably coupled to the pumping device (100). The infusion set may be removably coupled to the patch (110) or the infusion set and the patch may be formed within a single piece. The pumping device may comprise a sensor (hall effect sensor) (not shown) adapted to detect when the pumping device is correctly coupled to the infusion set. Said sensor is preferentially connected to the processor of the pumping device (100).

When the pumping device and the infusion set are correctly coupled, a fluidic pathway is created. Said fluidic pathway extends from the reservoir to the infusion site.

Figure 1D:
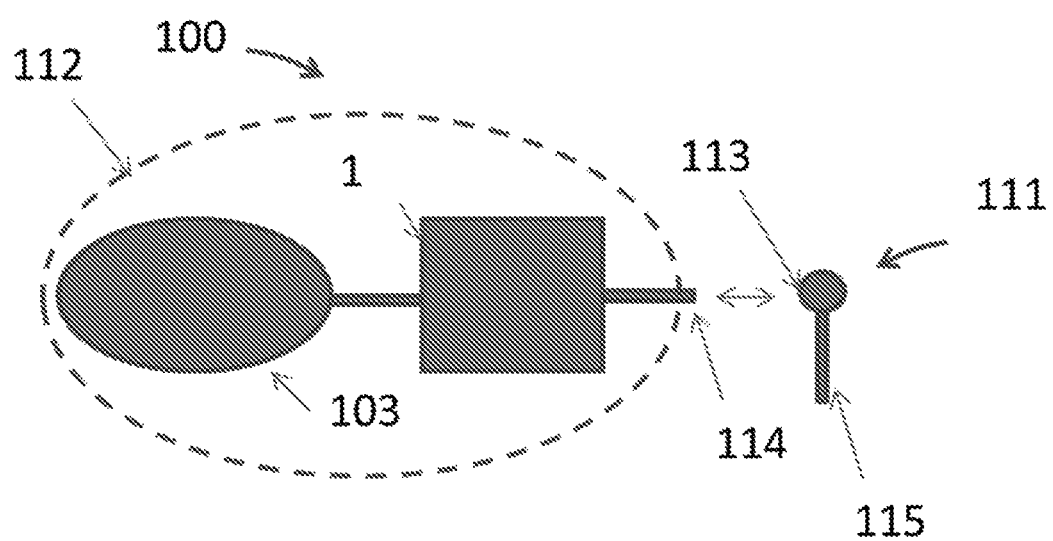

The FIG. 1*d* shows a schematic of the pumping device (100) which is disconnected from the infusion set (111). The pumping device comprises a housing (112) in which a reservoir and a pumping unit are arranged. The pumping device (100) further comprises an outlet port (114) adapted to be connected (in fluid communication) to an inlet port (113) of the infusion set (111) when the pumping device and the infusion set are coupled. Said infusion set further comprises a cannula (115), a needle or a micro needle.

Figure 1E:
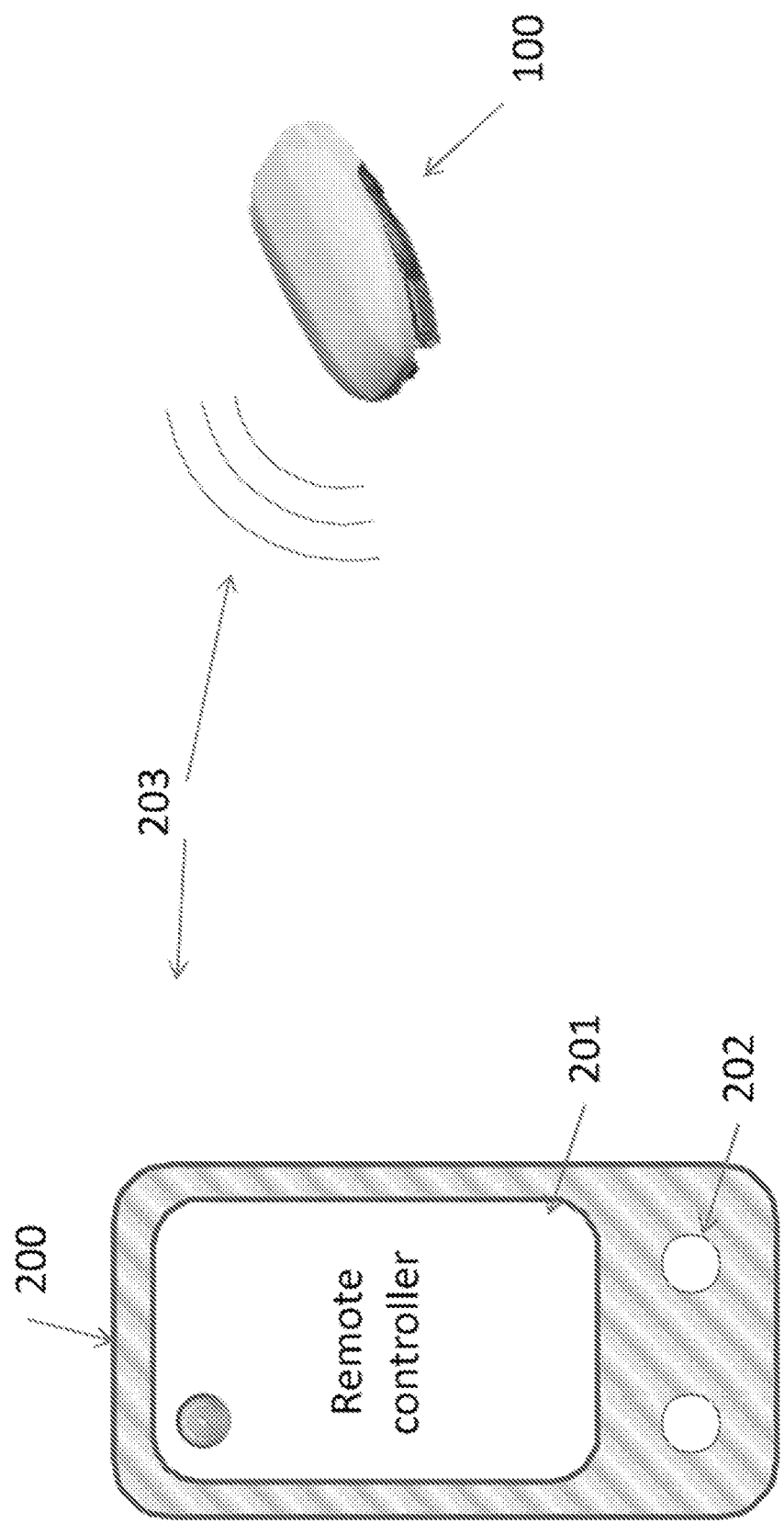

In one embodiment as shown in the FIG. 1*e*, the delivery system further comprises a remote controller (200). Said remote controller is adapted to command and program the pumping device (100) and it is used as an interface between a user and the pumping device (100).

The remote controller (200) comprises a screen (201) (for example a touch screen) and, optionally, at least one button (202). The remote controller (200) and the pumping device (100) comprise telecommunication devices (203) which allow exchanging data between the pumping device and the remote controller. At least one telecommunication device may be arranged in the housing of the remote controller or in the housing of the pumping device. Said telecommunication device exchanges data from the pumping device to the remote controller and from the remote controller to the pumping device via wireless communication (for example Radio Frequency, Bluetooth, WIFI, . . . ). Said remote controller may comprise a sensor for measuring an analyte level present in a body fluid (of the patient) (for example blood glucose level). The medical device may further comprise a remote sensor device secured against the patient skin wherein said remote sensor device is adapted to monitor for example the blood glucose level of the patient on a regular basis.

In one embodiment, the pumping device comprises an element adapted to limit the triggering of the alarm. Indeed, it may be appropriate to add a buffer compartment between the pump and the injection site, which is capable of retaining a certain amount of drug to be infused while increasing the pressure applied on the injection site (e.g. an elastic or elastomeric bladder or any elastic or elastomeric membrane, elastic or elastomeric tubing or reservoir), so that in case of an occlusion the pressure can be at least maintained if not increased until the occlusion is relieved. Alternatively, the pressure can also be at least maintained if not increased in case of a partial occlusion, so that the volume to be delivered can be actually delivered in a certain period of time, which is depending on the importance of such restriction. Since the pressure inside this compartment can also be monitored over time by the pressure sensor inside the pump (preferably the one placed after the pump), each following stroke of the pump can be actuated only by the time the pressure is getting back under a certain value (indicating that the previous delivered volume has been actually delivered to the patient). Such buffer would also improve the delivery of the volume contained in such reservoir, since the pressure is maintained at a higher level for a duration which is as long as needed until the volume is delivered to the patient, which is much longer than the time of the stroke itself, should there be a flow restriction or occlusion during such stroke.

Actuation Profile

As described above, the pumping unit comprises a pumping chamber. The volume of the pumping chamber varies depending on the actuation of the pump. An actuator exerts a force against the pumping membrane of the pumping chamber. Said actuator is controlled by the processor. The pumping membrane may comprise two well defined positions which are:

the top position, when the pumping membrane is fully pushed. In this position, the volume of the pumping chamber is minimal.

the bottom position, when the pumping membrane is fully pulled. In this position, the volume of the pumping chamber is maximal.

Preferentially, the pumping membrane further comprises another position called thereafter the rest position (position of the pumping membrane when the actuator is not energized) which may be substantially located between the top position and the bottom position. The elasticity of the membrane allows to the pumping membrane to come back at a substantially similar position when the actuator is not energized.

The processor of the pumping device controls the actuation profile. In one embodiment, the actuator is fed by a high positive or negative voltage (for example +/−200 Volts). In this case, the pumping device comprises at least one amplifier (supplied by the battery (109)) so as to reach said high voltage, said amplifier may be arranged into the non-disposable part of the pumping device connected to electronic elements of the device for example via a printed circuit board. In other case, the amplifier may be arranged into the disposable part of the pumping device.

The high negative voltage (respectively positive voltage) generated at the amplifier output may correspond to a pull (respectively push) movement of the pumping membrane, and as a consequence an intake (respectively infusion) of the liquid from the reservoir (respectively toward the patient). The effect of a positive or negative voltage on the piezo movement is directly driven by the initial polarization of each layer of the piezo. Therefore the upward movement of the piezo when biased with positive voltage is purely arbitrary. Different piezo configurations (bimorphs or multimorphs) having different polarization and different electrode configuration could achieve a downward movement when biased at high positive voltage.

Two distinct actuation profiles may be commanded by the processor.

Figure 11:
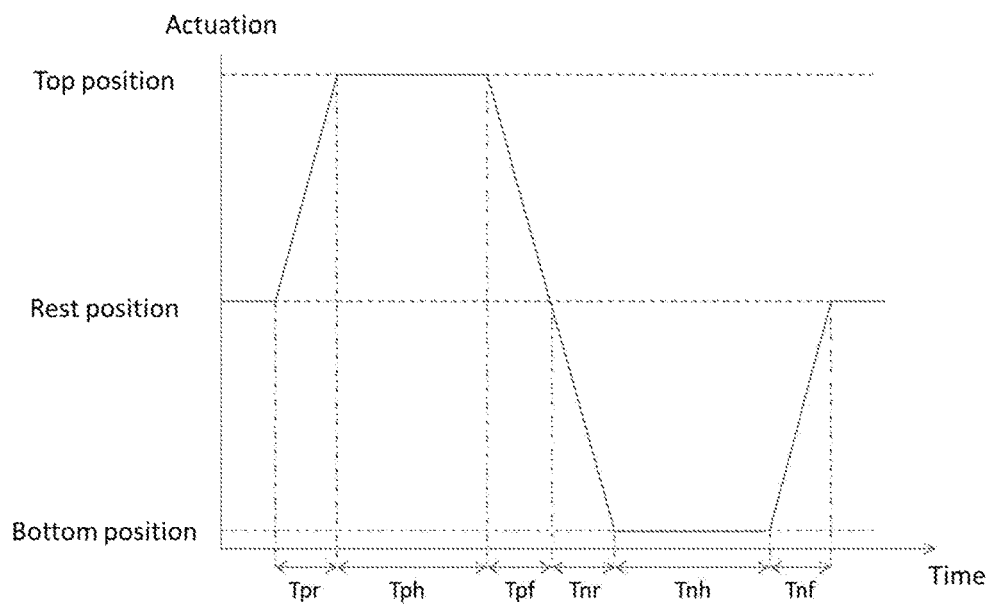
FIGS. 11 and 12 shows two distinct actuation profile.

A first actuation profile: Push-Pull-Push, preferentially partial push-full pull-partial push. A schematic of this actuation profile is described in the FIG. 11, it consist in a series of actuation of the actuator resulting in three steps:

1. A partial push which moves the drug from the pumping chamber to the patient (Infusion of the drug)
2. A full pull which moves the drug from the reservoir to the Pumping chamber (Sunction of the drug)
3. A partial push which moves the drug from the pumping chamber to the patient, until the pumping membrane returns in rest position (Infusion of the drug)

Figure 12:
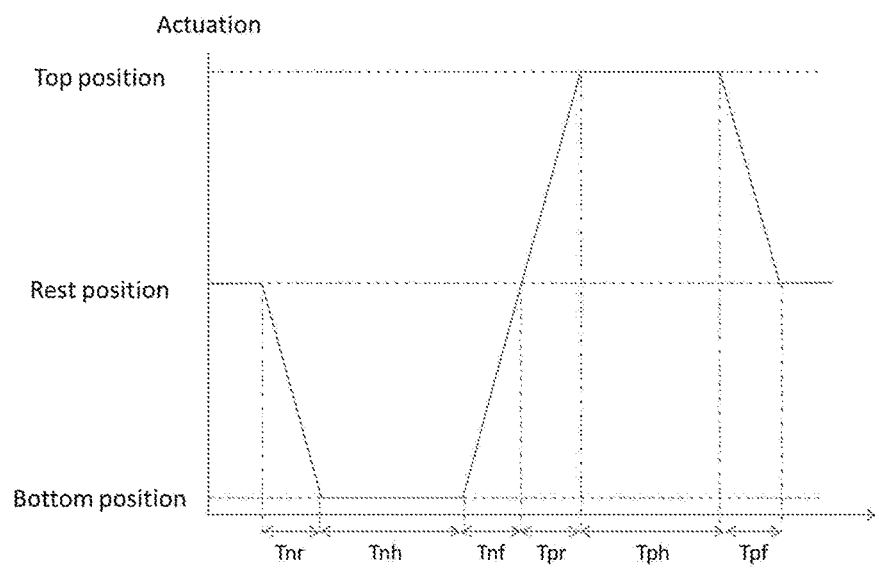

A second actuation profile: Pull-Push-Pull, preferentially partial pull-full push-partial pull. A schematic of this actuation profile is described in the FIG. 12, it consist in a series of actuation of the actuator resulting in three steps:

1—A partial pull which moves the drug from the reservoir to the Pumping chamber (Suction of the drug)
2—A full push which moves the drug from the pumping chamber to the patient (Infusion of the drug)
3—A partial pull which moves the drug from the reservoir to the Pumping chamber until the pumping membrane returns in rest position (Suction of the drug)

The first actuation profile may be called a standard actuation profile and the second actuation profile may be called a reverse actuation profile. The first actuation profile may improve the accuracy of the delivered amount of fluid because the last actuation is a push and not a pull. If the last actuation would be a pull, it increased the risk of suction of air bubble.

For each actuation profile, the actuator is supplied by electronic elements of the pumping device during a predetermined time period which may be:

Tpr is the time period during which the actuator is gradually biased with a high positive voltage (for example up to +200V). It corresponds to a partial push. During this time period, the pumping membrane moves gradually toward the top position.

Tph is the time period during which the actuator is biased with a substantial constant voltage (for example +200V). The pumping membrane reaches and is hold in a top position (which could be for instance a mechanical stop) during a predetermined time period.

Tpf is the time period during which the actuator is progressively powered down to a low voltage (e.g. 0 volt). It corresponds to a partial pull. During this time period, the pumping membrane gradually comes back to a rest position.

Tnr is the time period during which the actuator is gradually biased with a high negative voltage (for example −200V). It corresponds to a partial pull. During this time period, the pumping membrane moves gradually toward a bottom position.

Tnh is the time period during which the actuator is biased with a substantial constant voltage (for example −200V). The pumping membrane reaches and is hold in a bottom position during a predetermined time period, this bottom position could be for example a mechanical stop.

Tnf is the time period during which the actuator is progressively powered down. It corresponds to a partial push. During this time period, the pumping membrane comes back to a rest position.

Tnf+Tpr corresponds to time period necessary to gradually change the piezo voltage from −200 to +200V and therefore to allow the pumping membrane to achieve a full push movement (in particular during a reverse actuation profile). Tpf+Tnr corresponds to time period necessary to gradually change the piezo voltage from +200 to −200V and therefore to allow the pumping membrane to achieve of a full pull movement (in particular during a standard actuation profile). The movement of the pumping membrane is driven by the piezo voltage but also by other parameters like the valve pretensions and the external inlet or outlet pressures. Therefore the time necessary to achieve a stroke with the pumping membrane from the bottom to the top position depends on many parameters. The minimum duration of the idle state at +200V or −200V is fixed so as to achieve this full stroke independently from those external parameters cited above.

The delivery system may comprise at least one actuation profile stored in a memory (for example of the pumping device). The time periods of the actuation profile may be variable and may depend on the infusion mode, for example:

Basal, and/or
Bolus, and/or
Extended bolus.

A basal is an infusion mode which allows infusing of insulin at a predetermined rate during a long time period for example 24 hours. Said rate may be variable during said time period. A bolus is an infusion mode which allows infusing insulin during a short time period (few seconds), a bolus is faster than an extended bolus. An extended bolus is an infusion mode which allows infusing insulin during a time period determined by a user.

To infuse a basal, the pump is actuated according to one or more basal stroke. To infuse an extended bolus, the pump may be actuated according to one or more basal or bolus stroke. To infuse a bolus, the pump is actuated according to one or more bolus stroke. One stroke is a full actuation as described by the FIGS. 11 and 12, the amplitude of the actuation and/or the different time periods may be a set of parameters stored in the memory of the pumping device.

A basal stroke comprises a standard actuation profile (or a reverse actuation profile) in which Tnr, Tnf, Tpr and Tpf is substantially equal for example to 30 ms whereas Tnh and Tph is substantially equal for example to 300 ms.

A bolus stroke (also called short bolus stroke) comprises a standard actuation profile (or a reverse actuation profile) in which Tnr, Tnf, Tpr and Tpf is substantially equal for example to 30 ms whereas Tnh and Tph is substantially equal for example to 100 ms.

In other terms, Tnr, Tnf, Tpr and Tpf may be substantially similar for each actuation profile. Tnh and Tph of a basal stroke may be longer than Tnh and Tph of a bolus stroke. For example, Tnh and Tph of a basal stroke (or an extended bolus stroke) may be at least two times longer than the Tnh and Tph of a bolus stroke.

In one embodiment, the medical system (preferentially the pumping device) comprises at least two distinct actuation profiles. Both are used for delivering the solution and at least one of said at least two distinct actuation profiles is used to detected at least one infusion anomaly (for example an occlusion). A remote controller or input device (button on the pumping device) may be used to command an amount of solution (which is to be delivered). Said command is sent to the processor and the processor controls the actuateur with said at least two distinct actuation profiles so as to deliver and to monitor.

In one embodiment, the processor is adapted to monitor the voltage of the actuator. Thus, the processor controls and monitors the actuator so as to determine the smooth operation of the actuator. During Tpr, Tpf, Tnr and/or Tnf, the slope of the voltage may be monitored by measuring at time interval the voltage. The voltage may be also monitored during Tph and Tnh.

Signal Processing

The principle of the signal processing is based on the comparison between some critical values (for example pressure values), that are measured at different times of the actuation cycle, with reference values that are predefined by design or during the manufacturing or during a learning phase before the priming of the device (for the first use of the pumping unit).

Figure 13A:
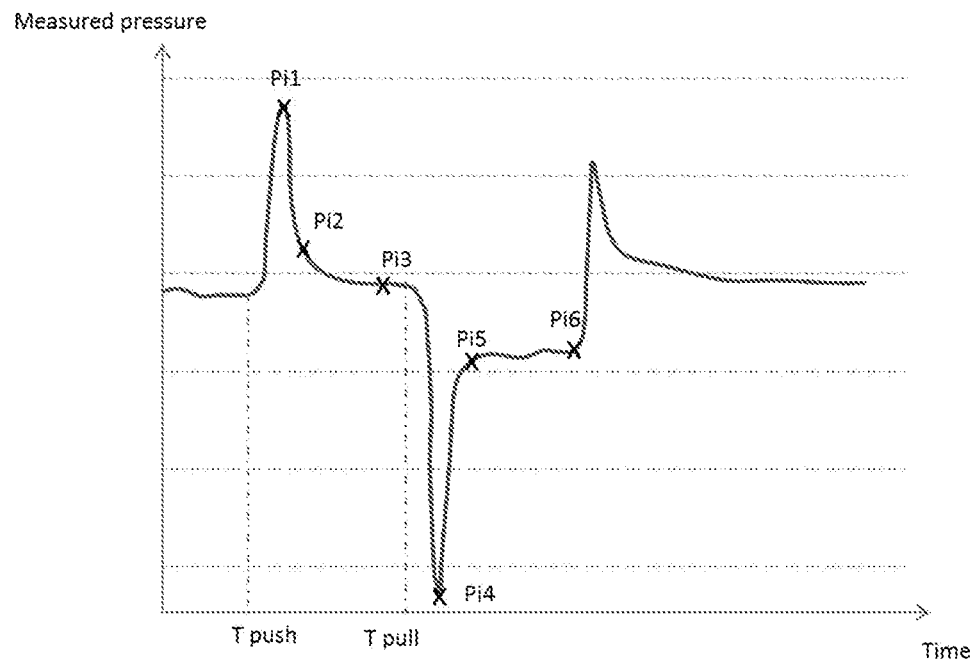
FIGS. 13a and 13b shows the "normal" pressure profiles of the inner and outer detector.
Figure 13B:
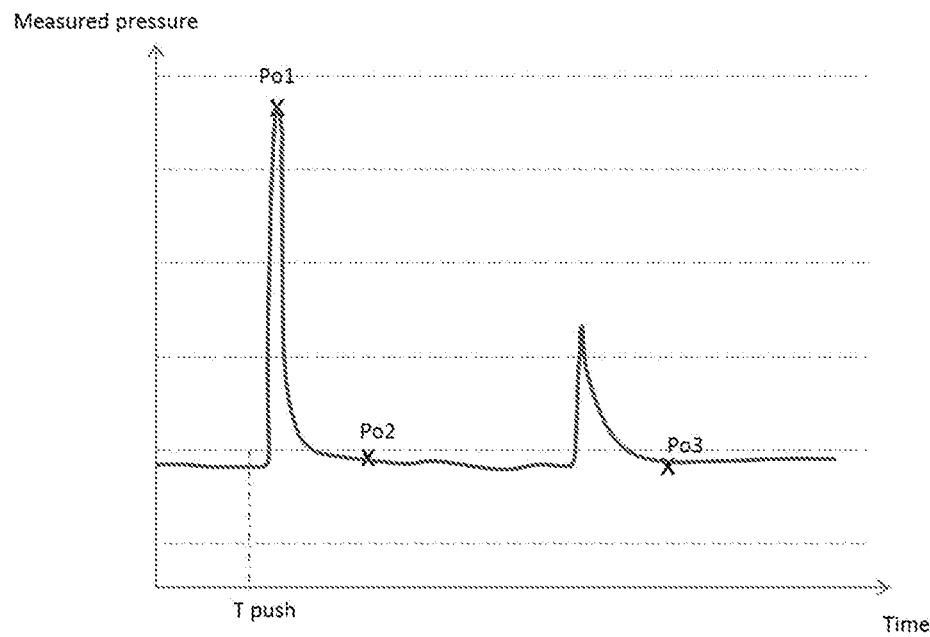

In FIGS. 13a and 13b, at least one measurement point for the inner detector and/or at least one measurement point for the outer detector may be used as references for the anomaly detections.

The out-of-stroke pressure measurement of both detectors at regular intervals of time is also needed to detect fault condition when the Pump is connected to the patient but at rest (not actuating) or to detect when an anomaly is removed (for example: occlusion released).

So as to simplify the signal processing, the reference is based on a standard basal stroke or a standard bolus stroke. Thus, during the actuation of the pump a standard basal stroke or a standard bolus stroke is integrated and used for the detection of the anomaly. For example, if the reference is based on a standard basal stroke (respectively a standard bolus stroke), during a bolus infusion (respectively basal infusion or extended bolus infusion), the actuation of the pump comprises at least one standard basal stroke (respectively a standard bolus stroke), for example one standard basal stroke for two or more bolus strokes (respectively for example one standard bolus stroke for two or more standard strokes).

Few examples of reference values are shown in the FIGS. 13a and 13b.

The reference values may be:

For the pressure sensor arranged in the pumping chamber (inner detector):

$Pi1 \rightarrow P_{push_{in}} = \max(P_{Din}(t), t_{push} \leq t \leq t_a)$ $Pi4 \rightarrow P_{pull_{in}} = \min(P_{Din}(t), t_{pull} \leq t \leq t_{a'})$ $Pi2 \rightarrow P_{ov\_0} = P_{Din}(t_b)$ $Pi3 \rightarrow P_{ov\_1} = P_{Din}(t_c)$ $Pi5 \rightarrow P_{iv\_0} = P_{Din}(t_{b'})$ $Pi6 \rightarrow P_{iv\_1} = P_{Din}(t_{c'})$ For the pressure sensor arranged downstream of the outlet valve (outer detector):

$Po2 \rightarrow P_{out\_0} = P_{Dout}(t_b)$ $Po3 \rightarrow P_{out\_1} = P_{Dout}(t_c)$ $Po1 \rightarrow P_{push_{out}} = \max(P_{Dout}(t), t_{push} \leq t \leq t_a)$ Wherein $P_{Din}(t)$ is the pressure measured at t time by the inner detector, $t_{push}$ is the moment when the push movement is triggered (in case of standard actuation profile for example at the start of the Tpr), $t_{pull}$ is the moment when the pull is triggered (in case of standard actuation profile, for example at the start of Tpf or Tnr). $t_{pull}$ and $t_{push}$ may be determined by the processor of the pumping device in accordance with the actuation profile. The durations (during a same stroke) are preferentially:

The duration $t_a$ (respectively $t_{a'}$) after the push triggering $t_{push}$ (resp. pull triggering $t_{pull}$) corresponds to the moment when the actuator stops to maintain the membrane in a determined position (resp. top and bottom positions). These durations $t_a$ and $t_{a'}$ may be equal to respectively to the sum of values Tpr+Tph (or Tnf+Tpr+Tph) and Tnr+Tnh (or Tpf+Tnr+Tnh).

The duration $t_b$ (resp. $t_{b'}$) after the push triggering $t_{push}$ (resp. pull triggering $t_{pull}$) corresponds to the moment when the outlet (resp. inlet) valve shall close if no anomaly occurs. These durations $t_b$ and $t_{b'}$, which are predetermined by design, for a given fluid viscosity, may be equal.

The duration $t_c$ (respectively $t_{c'}$) after the push triggering $t_{push}$ (resp. pull triggering $t_{pull}$) corresponds to a predetermined time after $t_b$ (respectively $t_{b'}$). Preferentially the duration $t_c$ (respectively $t_{c'}$) is a moment which satisfies ideally to the relation $t_b \leq t_c \leq t_a$ (resp. $t_{b'} \leq t_{c'} \leq t_{a'}$). In other words, when the valves are expected to be closed, the pumping membrane is maintained in a fixed position (top or bottom position) during a minimum duration $t_c-t_b$ (resp. $t_c-t_{b'}$) so as to allow the accurate monitoring of the pressure within the pumping chamber normally closed.

If Tpr, Tpf, Tnr and Tnf are each substantially equal to 30 ms and if Tph and Tnh are each substantially equal to 300 ms, then $t_a$ may be equal to 330 ms, $t_b$ may be equal to 100 ms and $t_c$ may be equal to 300 ms. Preferentially, $t_a$, $t_b$ and $t_c$ are different predetermined moments during the stroke.

$t_a$, $t_b$ and $t_c$ may be determined during the manufacturing or by the designer, or determined depending on the pretension of the valve, on the actuation profile or on the boost sequence (for example during a learning phase).

The pressure differential between Pi2 and Pi3 is directly affected by valve leakage or downstream occlusion.

Test During the Boot Sequence

As described above the pumping device comprises a disposable part and a non-disposable part. The disposable part comprises all elements which are in contact with the fluid (for example the drug). When the non-disposable part is fixed with a new disposable part, the processor launches a boot sequence in order to (at least one of the following list):

check if the pump is empty,
measure the pressure sensor offsets
measure the valve(s) pretension
check that the offsets and the valve(s) pretensions are within specifications, in order to ensure that the disposable unit is not damaged or under abnormal reservoir pressure conditions.

Figure 14:
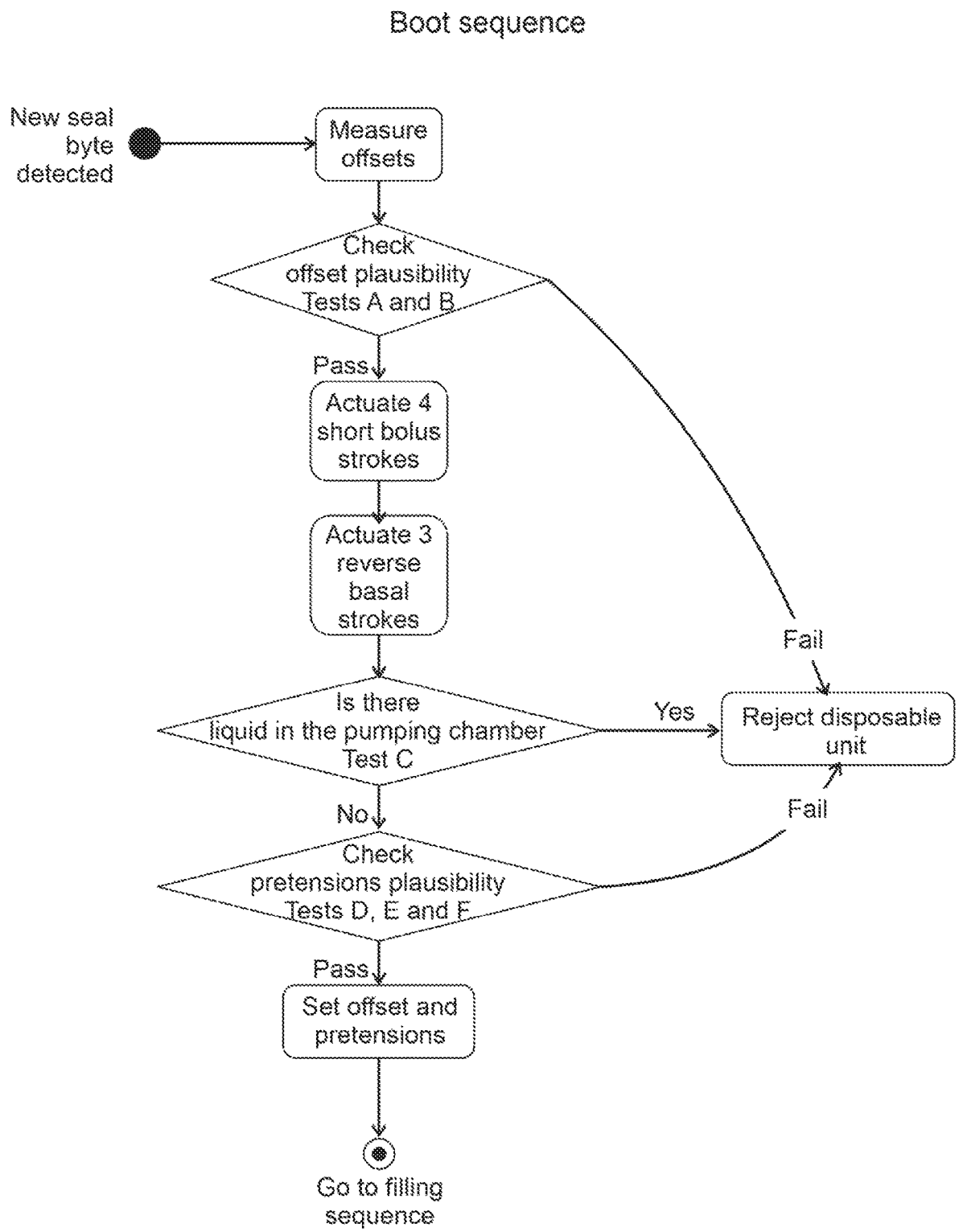
FIG. 14 shows the flowchart of the boot sequence.

The workflow of the boot sequence is show in the FIG. 14.

The pumping device starts the boot sequence by measuring the offset. The offsets (and especially the inner detector offset) shall be measured immediately after the disposable connection, in order to ensure the measurement is not altered by a pressure variation that could occur when the user fills the reservoir. The measurement should be averaged over at least 1 second to reduce the measurement noise.

After the measurement, the processor checks the offset plausibility (the offset shall be within the predefined acceptance limits). If the measurement is within the acceptance limits then the boot sequence can continue. But if it is out of range, an indication device may alert the user and the disposable part has to be discarded.

After this test, the pump is actuated with a predetermined number of bolus strokes which may be followed by a predetermined number of reverse basal strokes so as to determine if the pumping chamber is already filled with liquid. The test C compares the pressure peaks Pi1 and Pi4 and the difference has to be less than a predetermined value. If test C fails then it is assumed that the pumping chamber is already fill with a liquid and thus this disposable part has already been used, the user is alerted and the medical system prompts the user to change the disposable part.

In case the pumping unit comprises a check valve which has a pretension, the tests D, E and/or F have to be performed so as to check the pretensions plausibility. The test D compare Pi2 and Pi5, the difference has to be within a reference range. The test E verifies that Pi5 is greater than a reference value and that the measurement of the offset is less than another reference value. The test F compares Pi2 and the measurement of the offset and ensure they are within a reference range. If the tests D, E and/or F fail then the processor may conclude one of the following possible causes: valve stiction, valve leakage, electrical failure, reservoir overfilling before measurement. The medical system may prompt the user to change the disposable part. The processor of the medical system may store this anomaly in the memory (for example of the remote controller or of the pumping device) and if at least one of the tests D, E and/or F with the new disposable part fails again for the same reason then the medical system may prompt the user to check the electrical contacts between the disposable part and the non-disposable part.

Filling Sequence

In the case where the reservoir is not prefilled, after the boot sequence the medical device may prompt the user to fill the reservoir. The processor may actuate a stroke (for example a reverse basal stroke) so as to detect liquid in the pumping chamber, if liquid is in the pumping chamber then the medical system increases the priming counter of an amount which is substantially equal to the volume of the pumping chamber when the pumping membrane moves from bottom to top or top to bottom positions.

The pressure sensor (for example the inner detector) of the pumping unit may monitor the pressure when the user is filling the reservoir. If the pressure reaches a predetermined threshold, the medical system may alert the patient and prompt him to stop the filling.

The device could be actuated during the filling phase in order to monitor with more accuracy the reservoir pressure (the inner detector being in direct communication with the reservoir pressure when the inlet valve opens, during a pull movement of the pumping membrane).

An indication device (audio or tactile, or visual) of the pumping device (or of the remote controller) may indicate the level of the reservoir or of the overfilling. For example, in case of a pulsated audio signal which is emitted when the patient starts to overfill the reservoir, the frequency of the pulsation may increase or an overfilling screen may be displayed on the screen of the remote controller . . . .

Priming Sequence

Figure 15:
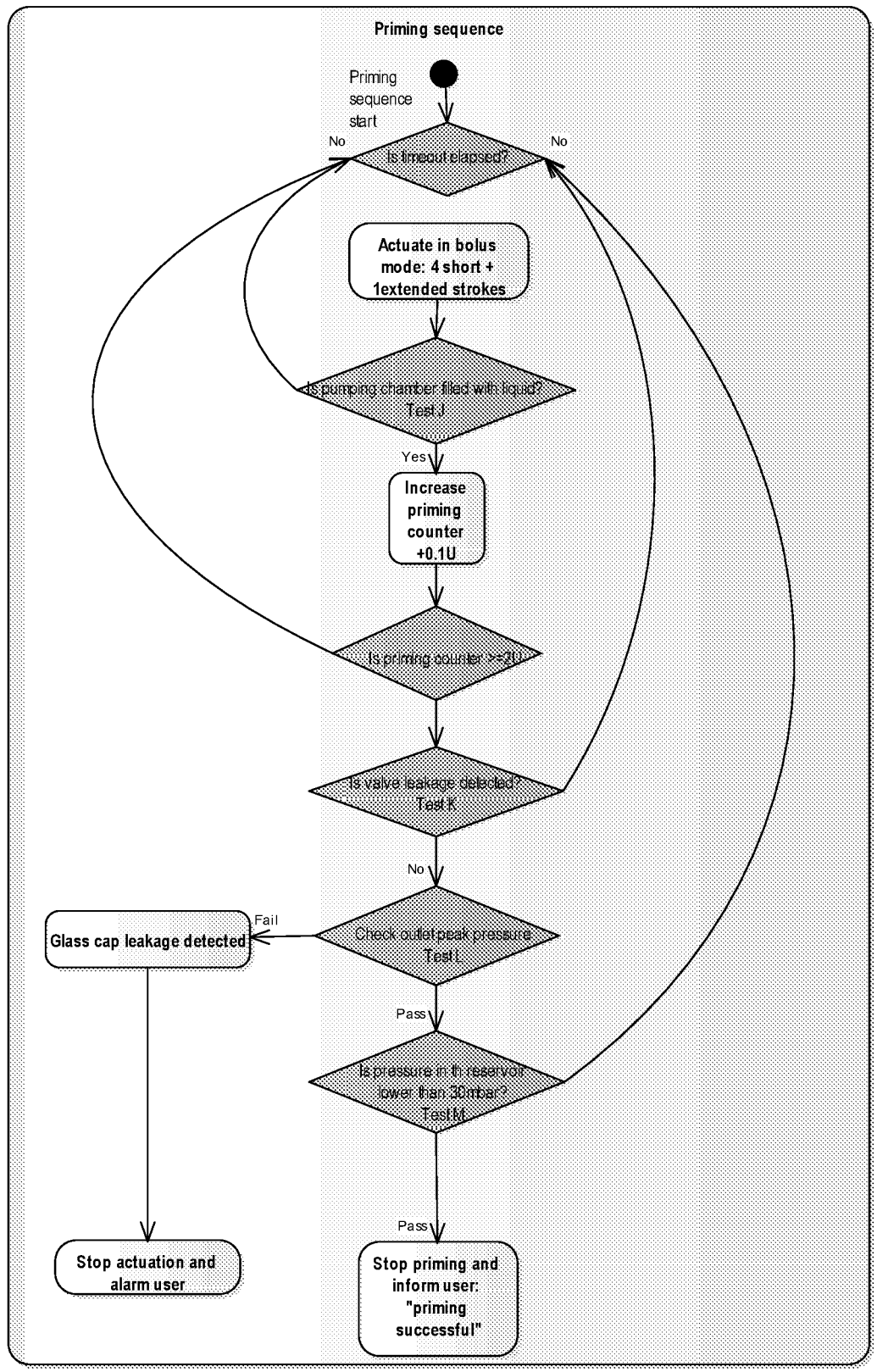
FIG. 15 shows the flowchart of the priming sequence.

The priming sequence workflow is presented in FIG. 15.

As described above, the pumping device may be patch pump which configured to be secured on the skin of the patient, for example via a specific patch coupled with an infusion set. The pumping device may comprise a sensor (for example Hall effect sensor or any other proximity sensors) which sends a signal to the processor when the pumping device is correctly fixed or coupled to the patch or to the infusion set.

Before priming the pump, the processor has to verify that the pumping device is not coupled to the infusion set thanks to the specific sensor. In other case, the medical system may ask to the user to check if the pumping device is or not coupled to the infusion set and, in case of connection, to disconnect it.

During the priming, the pump is actuated in bolus mode. Since the pressure profile is different when the pump moves air or liquid, the processor monitors the pressure until the difference between Pi1 and Pi4 reaches a threshold. Once the liquid is detected, the Pump continues to actuate in bolus mode to fill the rest of the pump down to the pump outlet, for example until a first drop appears at the Pump outlet. The user can indicates to the medical system that the priming is ended or the processor actuates a predetermined number of strokes.

The priming may be performed at higher frequency than a bolus to reduce the priming duration. In particular the actuation frequency could be increased during the early phase of the priming, when the pumping chamber is full of air. As soon as the drug enters into the pumping chamber the actuation frequency could be lowered (e.g. up to the stroke bolus or basal frequency) to secure the pumping accuracy.

Then, the final step of the priming phase consists in checking the pressure signal to ensure the reservoir is not pressurized, and the Pump is functional. In case of failure, the pump continues to prime until failure disappears or until timeout. This phase ensures the pressure in the reservoir at the end of the Priming phase is below a predetermined value. In other terms, if the reservoir is pressurized, the pump is actuated so as to remove the over pressure from the reservoir to prevent any free flow (of the drug from the reservoir to the patient).

Detection of Occlusions

Occlusion is a common failure for infusion device such an insulin pump. Occlusion is typically due toto the aggregation of insulin fibrils at the outlet, a kinking of the cannula or a compression of the skin around the infusion site, or even a tissue reaction limiting the diffusion of the drug. An occlusion leads to two kinds of risks:

Hyperglycemia: during the occlusion itself, since there is no infusion of insulin Hypoglycemia: at or during the release of an occlusion (e.g. if the compression of the skin around the infusion site or the kinking of the cannula is suddenly released) there is a major risk of over-infusion because the accumulated amount of insulin that has not been injected during the occlusion is injected very quickly upon release of the occlusion condition. In particular, when the pumping unit uses a cartridge with a piston, most of the time the pumping device does not detect immediately the occlusion and the pumping unit continues to push the insulin. The force may increase until the occlusion is released, causing an important amount of insulin that has been accumulated over time to be delivered too quickly. In particular, in case of non-detected occlusion, there is a major risk that the patient decides to do a compensation bolus if he measures a high blood glucose level. The patient may receive twice the bolus dose after release of the occlusion.

The occlusion detection is therefore a key factor for the patient safety.

This occlusion may be due to:

The cannula (cannula kinking, quality of the cannula, ageing of cannula, . . . )

An inflammation near the infusion site

A tissue reaction around the cannula (which tissue reaction usually only occurs after a certain time of use)

The emergence of a nodule or a mechanical tissue reaction

The position of the patient (for example if the patient sleeps on the infusion site)

An action of the patient (for example when the cannula is placed into a muscle which is contracted)

Thanks to the design of the pumping unit such as disclosed above, the device exhibits a very low compressibility and any occlusion will induce a large increase of the outlet pressure which could be detected by one or both detectors. The pressure sensor located downstream of the outlet valve is in direct fluid and pressure communication with the infusion site (i.e. without any valve in-between or substantial flexible or compliant tube between the pump and the infusion set) and this sensor is preferably used to monitor occlusion (partial or total). A total occlusion will be detected during the first actuation that follows the event, an alarm can be triggered to prevent the generation of large pressure that may damage the fluidic line and/or a suspended mode may stop the pumping unit until the occlusion is released.

A partial occlusion draws at least one specific pressure profile, thus the processor can easily detect this event and distinguish it from a total occlusion. It has to be noted that in the devices of the prior art (for example which uses a cartridge with a piston), the occlusion event is detected when the pressure reaches a threshold, thus it is impossible to distinguish a total occlusion from a partial occlusion.

Partial occlusions have been experimentally studied by attaching after the cannula small tubings of different lengths, from 10 to 40 cm, with an internal diameter of 0.09 mm (tubing ref. 1578 from Upchurch Scientific) creating fluidic restrictions. These restrictions exhibit fluidic resistances about 2 orders of magnitude larger than the pumping mechanism itself.

Figure 2:
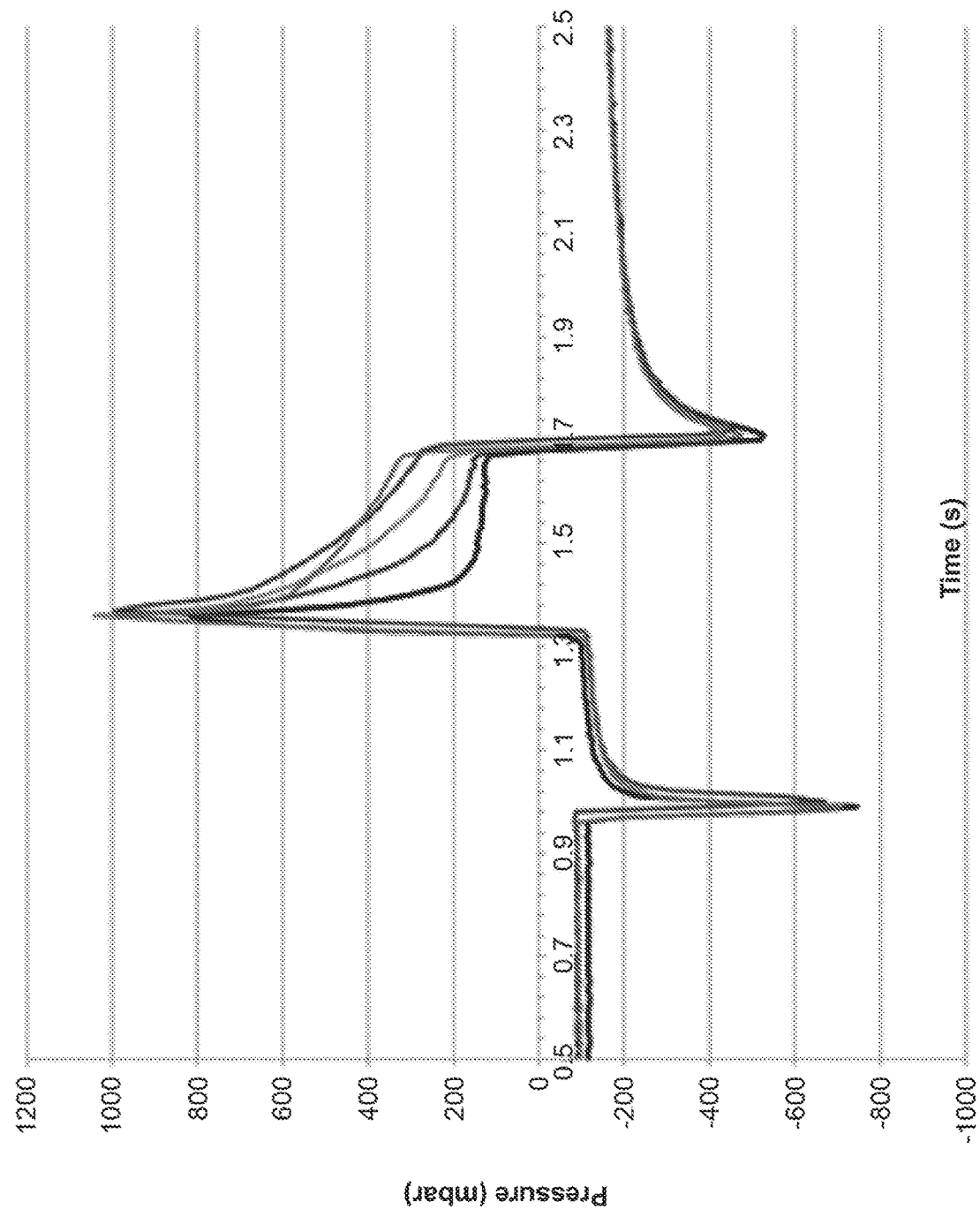
Figure 3:
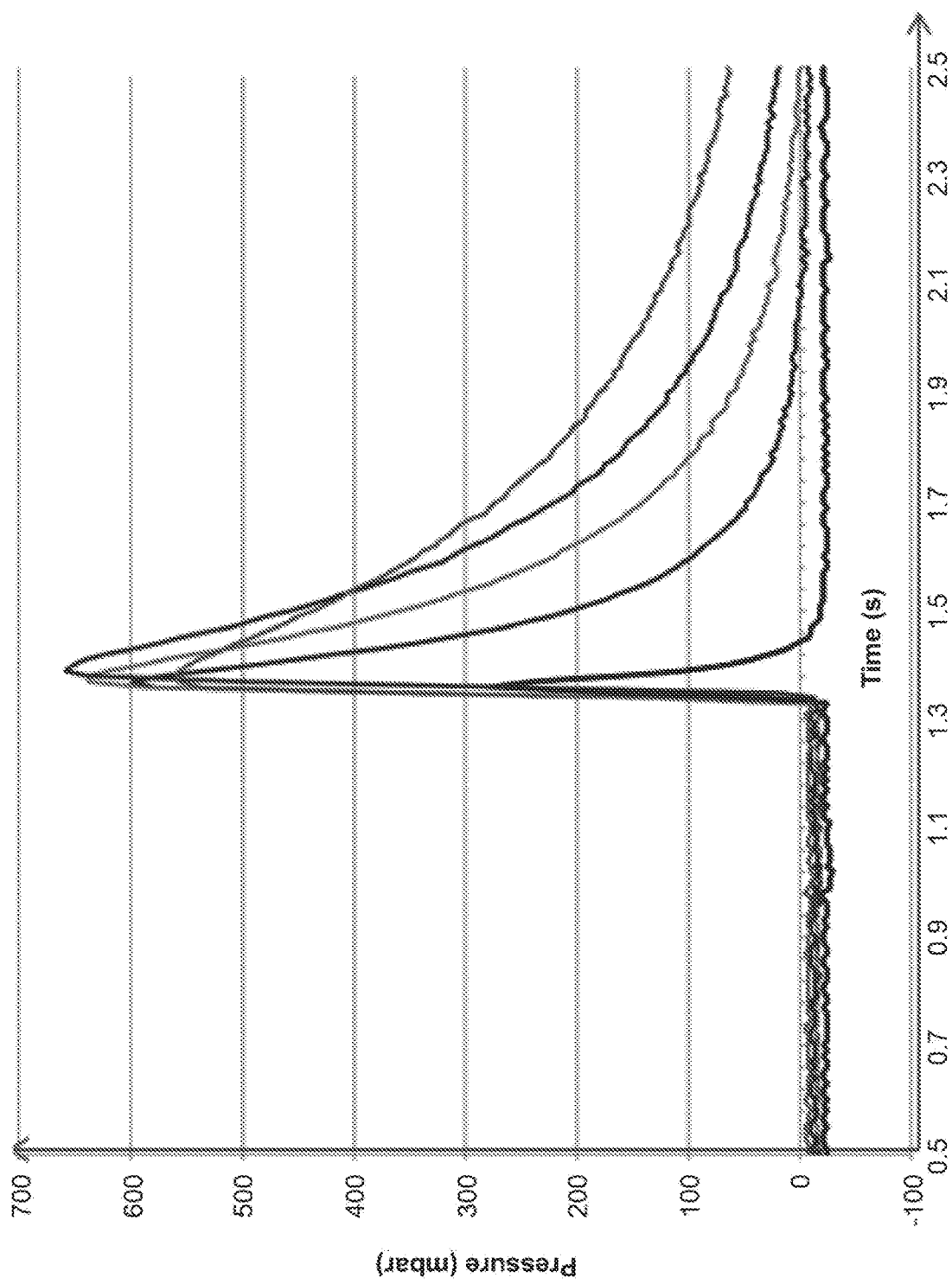

The stroke volume is measured with the precision scale. The inner and outer detector signals in fast basal mode (at 10 U/h, which is the highest programmable basal rate, equivalent to 100 microliters of insulin per hour or one stroke every 7.2 seconds) are shown in FIGS. 2 and 3 respectively.

A fluidic restriction equivalent to a tubing of ID 0.09 mm and 30 cm in length (>1E16 Pa·s/m3) leads to an under-delivery larger than 5% at a high basal rate (10 U/h). The stroke volume decreases slowly when the tubing length increases, respectively 206 nl, 200.4 nl, 196.1 nl, 187.1 nl and 182.3 nl for tubing of 0 cm, 10 cm, 20 cm, 30 cm and 40 cm.

Figure 4:
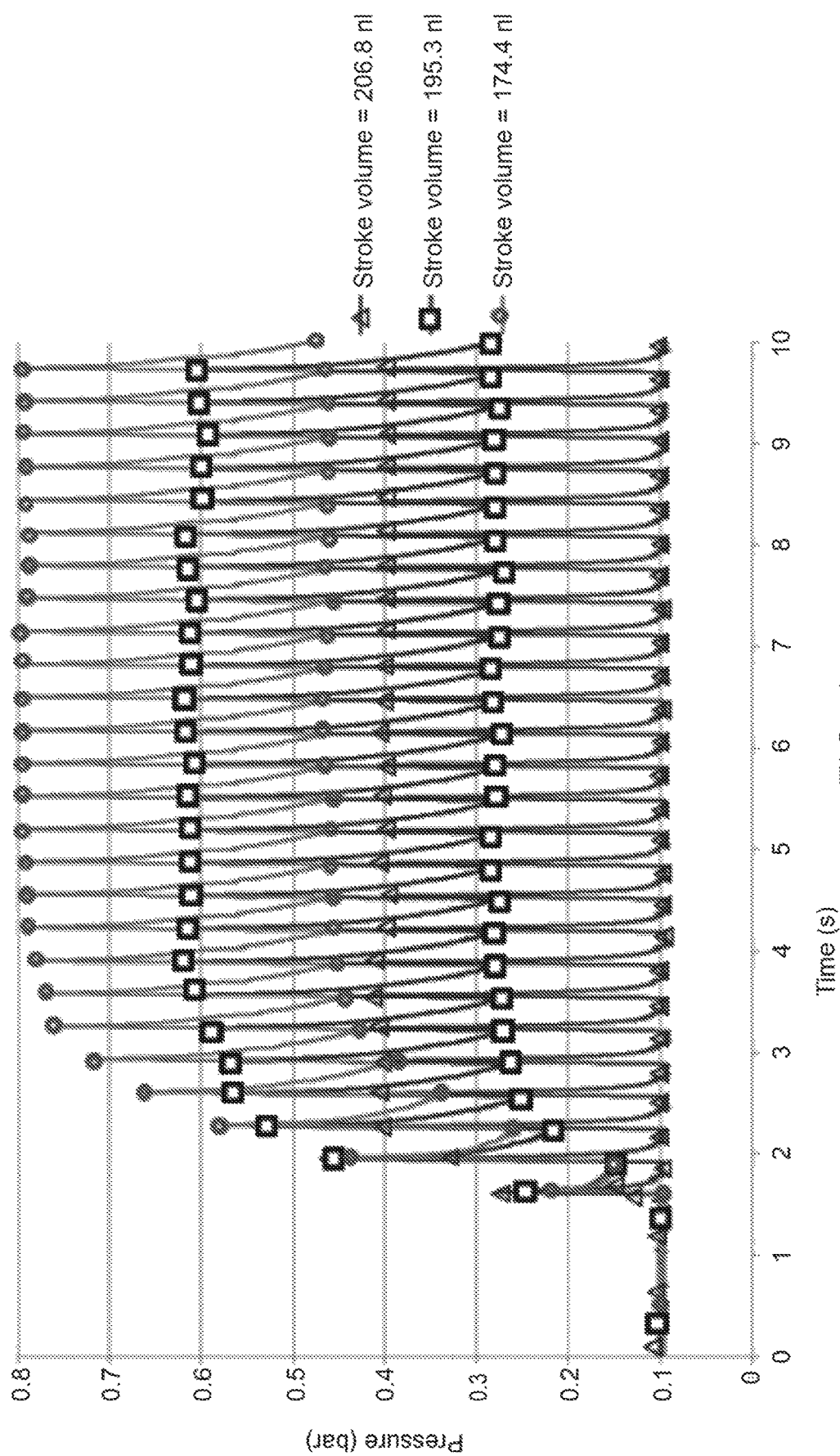

In bolus mode (equivalent to 225 U/h with 1 U of insulin U100 is equal to 10 microliters) the effect of these partial occlusions on the downstream pressure (measured with the outer detector) is shown in FIG. 4 using no tubing for the reference and tubing of 10 cm and 20 cm. The indicated stroke volume has been averaged over 50 strokes. As for basal rate, partial occlusion can be easily detected from the first stroke following the fluidic restriction, but the criterion used to trigger under delivery alarm shall be again based on a threshold pressure at the end of each actuation cycle, this threshold being correlated to a loss larger than 5% of the nominal stroke volume.

Figure 17:
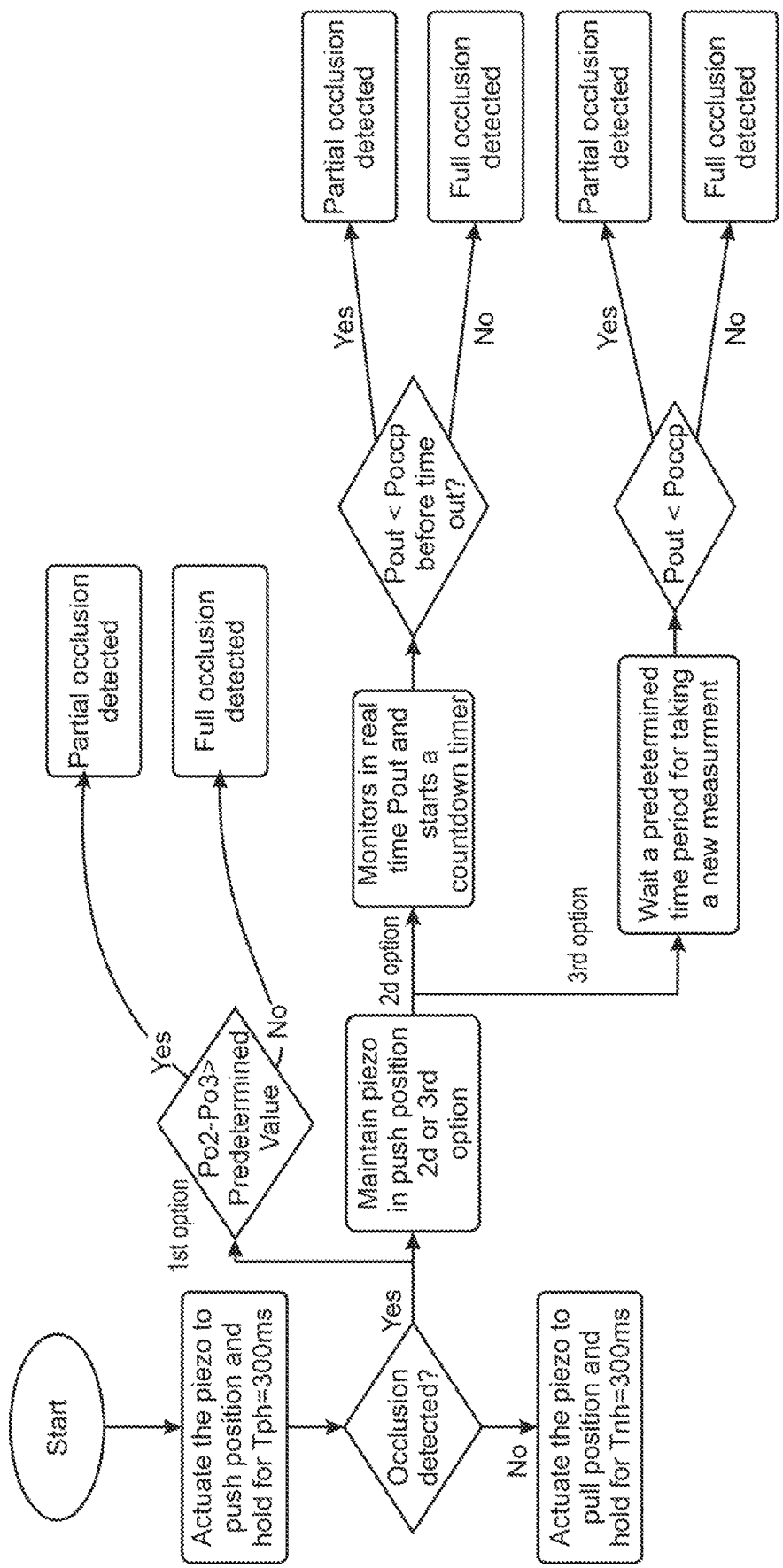
FIG. 17 shows the flowchart for distinguishing a partial occlusion from a total occlusion.

The FIG. 17 shows the workflow of the occlusion detection. A standard basal stroke may be used as reference to detect an occlusion and at least one measurement is taken during the stroke. In particular, the actuator is actuated so as to perform a push movement and is maintained at high voltage during a predetermined time period (for example Tph). During this predetermined time period, the pumping unit measures at least one fluid pressure $P_{out}$ (for example Po3) by a pressure sensor in the fluidic pathway (preferentially the outer detector). The processor compares Po3 to a first predetermined value (Pocc). If Po3≥Pocc then an occlusion is detected. Once the occlusion is detected, the processor may control the pumping unit in order to determine if the occlusion is partial or total. Three options are possible (for example during the current stroke):

the processor compares Po2 and Po3 (in the same stroke), if the difference is greater than a predetermined value then the occlusion is partial; Or the processor maintains the actuator in push position until $P_{out}$ decreases and reaches a predetermined value Poccp. Poccp may be less than or equal to Pocc. If the fluid pressure falls below Poccp then the occlusion is partial. Preferentially, a timer is launched so as to stop the step after a predetermined time period; Or the processor maintains the actuator in push position during a predetermined time period (for example 2 second) which is greater than Tph and if at the end this time period Pout≥Poccp then the processor concludes to a full occlusion.

The measurements may be temporary stored in a memory.

The main drawback of the second option is that it requires processing a too large amount of data and thus it (piezo and/or processor) consumes too much energy.

Once a partial occlusion is detected, the actuation profile may be modified (as described below).

Under-Delivered Counter

In one embodiment, the processor of the medical system (preferentially of the pumping device) is adapted to monitor the amount of the solution which should have or has been delivered and stores this data in a memory. Thus, the processor comprises at least one counter which counts the amount of solution which is:

delivered; or, under-delivered; or, potentially under-delivered or not delivered Thanks to this at least one counter, the medical device may inform the patient or the caregiver of the effective delivery.

This counter may be incremented at each stroke. For example, if a stroke corresponds to an infused amount equal to 0.1 U, at each stroke, the processor may increment a specific and dedicated counter which correspond at the infused amount. A full stroke may corresponds of ten times one increment. Thus, if an anomaly infusion occurs (for example a full occlusion) or if the suspended mode is enabled, the processor adds a number of increment which correspond of undelivered or under-delivered amount in the specific counter (at each stroke which should have been actuated or has been commanded by the processor).

In one embodiment, the system comprises only one counter and the processor is adapted to estimate the amount of under or undelivered stroke. For example, if the pump has to actuate 30 strokes but the counter of delivered strokes have an information corresponding to 20 strokes effectively delivered, the processor may dedicate or compute the number of undelivered stroke, for example 10 strokes, based on the counter of delivered strokes.

In one embodiment, the medical system comprises at least two of the following counters: a counter of delivered strokes, of potentially under-delivered strokes, of under-delivered strokes or of undelivered strokes. At each stroke, one of these counters may be incremented by a determined number of increment depending on the effective delivery. If no occlusion is detected, then the processor may add a determined volume in the counter of delivered strokes. If an anomaly infusion is detected but the processor cannot precisely determine the delivered volume, then the processor may add a given volume in the counter of potentially under-delivered strokes. But if the processor can estimate the delivered volume then the processor may add said volume (the effective under-delivery) in the counter of under-delivered strokes. For example, since no solution can be infused in case of full occlusion, the processor precisely determines the volume of solution of this stroke which is not delivered and increment the information in the counter of undelivered strokes. But in case of partial occlusion, a part of the stroke volume may be infused, thus the processor may add said stroke volume to the counter of potentially under-delivered strokes.

In one embodiment, the medical system used the fluid pressure signal to determine the counter. For example, if the signal reaches a full occlusion threshold (for example Po2 or Po3>500 mBar) then the counter of under-delivered strokes is incremented. If the signal reaches a partial occlusion threshold (for example Po2 or Po3>200 mBar) then the counter of potentially under-delivered strokes is incremented. The full occlusion threshold may be larger than the partial occlusion threshold.

Nevertheless, as described below, since the pumping device may force the delivery (for example by maintaining the pumping membrane in top position in case of partial occlusion), the processor may detect a partial occlusion but the pumping device in fact infuses the whole of the stroke volume (the stroke volume being the volume which can be infused by a stroke). In this case, the fluid pressure may decrease under a threshold (for example under the partial occlusion threshold) and the processor may add this volume in the delivered counter.

In one embodiment, when the occlusion has been released, the medical system may propose or suggest or prompt to the patient to infuse the amount of the counter of under-delivered strokes and/or the amount of the counter of undelivered strokes and/or counter of potentially under-delivered strokes.

In one embodiment, when the occlusion has been released, the medical system tries to automatically infuse the amount of solution which is in the counter of under-delivered strokes and/or in the counter of undelivered strokes.

In one embodiment, if the counter of undelivered strokes or under-delivered strokes or potentially under-delivered strokes or the sum of at least two previous counters reaches a predetermined amount, an alarm is triggered so as to inform the patient. Said predetermined amount of under delivery may be set by the patient or by the caregiver via a specific screen of the remote controller.

In one embodiment, when the patient wants to command a bolus, the medical system may indicate to the patient the amount of under delivery. For example, the screen of the bolus command comprises an area in which the amounts of the counter of under-delivered strokes or potentially under-delivered strokes or the sum of both counters are displayed. In this case, the patient can add this amount to the new bolus.

These counters may be reset at zero after changing the disposable unit or after the next commanded bolus, or after a given time period that may be preset by the patient or the caregiver.

Add Test for Anomaly Confirmation

In one embodiment, the system may validate a first interpretation of the pressure profiles of both detectors using detection algorithm or an assumption by actuating the pumping mechanism. Thus, when an over pressure is detected by the first pressure sensor (e.g. in the pumping chamber), the processor can command at least one additional stroke and check the profile of this stroke. In particular, the data of the second pressure sensor may be monitored. Thus, if the second pressure sensor detects also an overpressure, then the processor confirms the presence of an occlusion in the fluidic path after the pumping chamber (or in particular downstream the outlet valve or second sensor) but if said sensor does not detect such an overpressure, then the processor imputes the overpressure detected by the first sensor to the reservoir overpressure.

Figure 18:
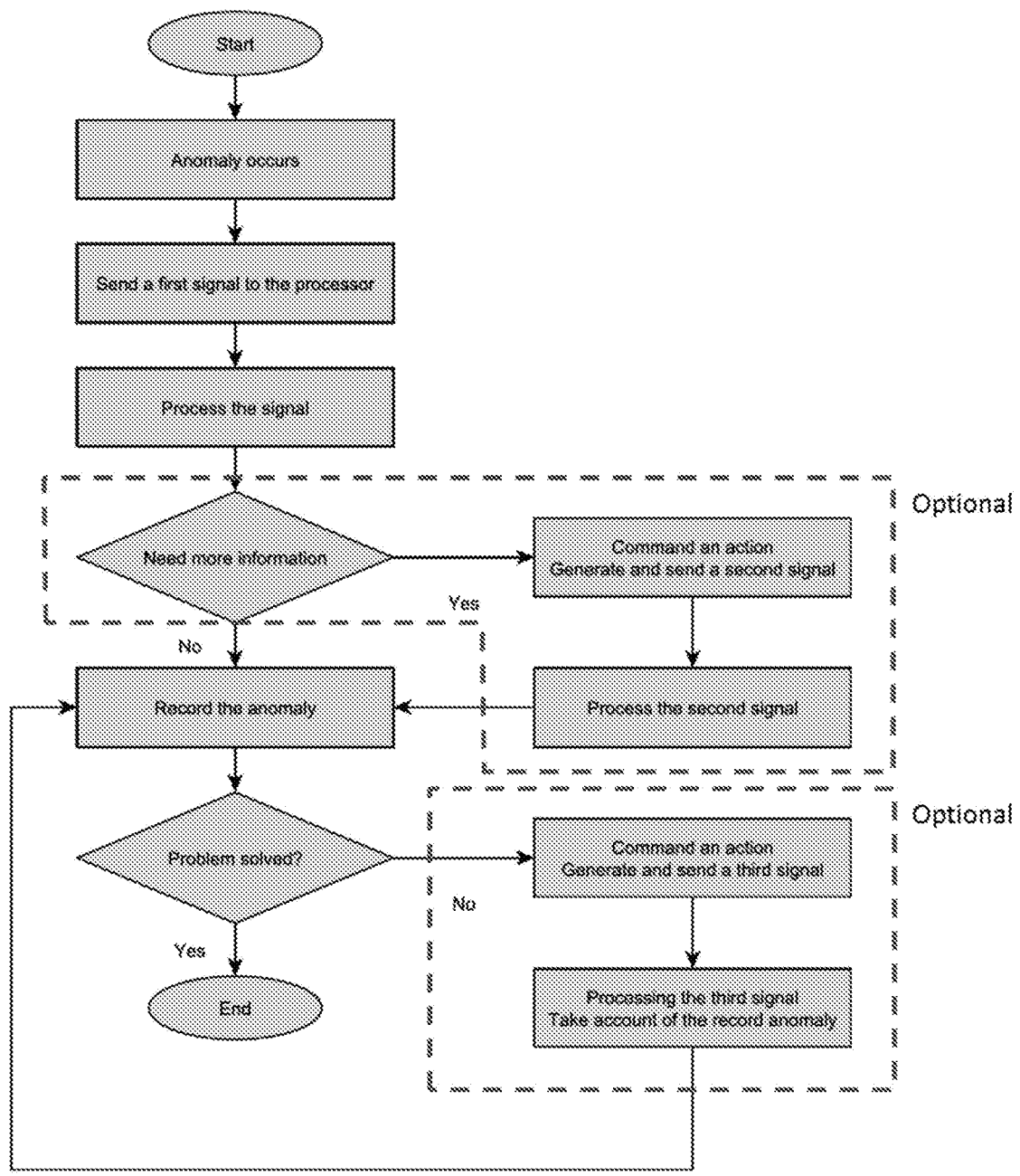
FIG. 18 shows the flowchart when an event is detected.

The FIG. 18 shows an example of flowchart. To check a potential infusion anomaly, the system performs the following process comprising:

Detecting an potential infusion anomaly,

Actuating at least one additional time the pumping mechanism,

Monitoring the pressure measured by a pressure sensor

Analyzing the monitored pressure profile

Confirm, refute or refine the nature of the detected failure

In the case where the system comprises a first pressure sensor arranged in the pumping chamber and a second pressure sensor located downstream of the outlet valve, if the potential infusion anomaly is an over pressure measured by the first pressure sensor then during the additional stroke, the processor will monitor the second pressure sensor. If the second pressure sensor detects:

An over pressure then the processor concludes that the potential infusion anomaly is an occlusion which is located in the fluidic pathway located downstream of the outlet valve (leading to underdelivery).

No over-pressure then the processor concludes that the potential infusion anomaly is an over pressure located in the reservoir (leading potentially to overdelivery).

Said additional stroke may be a standard or reverse basal or bolus stroke and the processor may take into account the delivered amount of fluid by this stroke. This verification may be used to check if the previously detected anomaly is removed at a predetermined time interval. The medical system may take into account this additional delivery and the processor may check that the additional delivery is not unsafe for the patient, otherwise an alarm may be triggered.

Monitoring of Successive Anomalies

As described above, the system may comprise a disposable unit and a reusable unit ("non-disposable" unit). The disposable unit is adapted to be physically and temporary attached to the reusable unit. The reusable unit may be used with several disposable units over time.

The disposable unit may comprise a fluidic block, the reservoir, a battery and an outlet. A reusable unit may be assembled by the patient to a disposable unit. Said battery may be a zinc-air battery needing oxygen. Thus, the housing of the system comprises a vent. Said vent may comprise a hydrophobic filter or coating in such a way that only gas can pass through the vent, while water or oil or any liquid cannot, in normal conditions of use.

In one embodiment, the system comprises a capacitive sensor in such a way to detect when the device is immerged. Preferably, the capacitive sensor is located near the vent. Thus, if the sensor is wet the system may prompt the user to check the vent, optionally after a predetermined time. The event may be recorded in a memory. The processor may monitor the current or voltage of the battery at time intervals (different or same time intervals) and if the battery depletes too quickly, the medical system may prompt the user to verify the vent.

In other cases (with or without immersion), if a first battery is depleted, then the system may prompt the user to change the battery (or with or without the housing in which the battery is arranged) but if two successive batteries discharge too soon, the processor can detect and suggest that a vent is probably clogged. Thus the system prompts to check the vent or change the housing comprising the vent. In other terms, the system records the first anomaly and if two successive events occur then the processor tries to solve the problem in a smart way.

Operating Mode

As described above, the processor may control the actuator to infuse a solution to a patient, to verify proper operation of the device or to find an anomaly. Once an event is detected, the medical system may be adapted to change the operating mode.

Suspended Mode

In one embodiment, the system comprises a suspended mode (also called safe state mode) which is automatically activated by the processor when a specific event occurs and an optional indication device may alert the patient about the status of the pumping device. The safe state mode or the suspended mode is an operating mode of the system wherein the system does not infuse fluid to the patient but computes the amount of fluid which should have been infused. The processor automatically switches in this operating mode when an infusion anomaly occurs. For example, if the processor detects an occlusion and/or if the overpressure generated by this occlusion is larger than a predefined value, the processor switches in suspended mode in such a manner as to avoid any potential damages to the pumping device and the indication device may prompt the user to change the infusion site, to apply a pressure on or to massage the infusion site.

In another case, the suspended mode may be proposed by the indication device and the user validates or not the suspended mode.

In one embodiment, the system, if and when it detects that the partial or total occlusion is removed or when the conditions leading to the under-delivery are released, will leave its suspended mode and resume therapy. Optionally, the system will calculate the amount of fluid it was assumed to deliver during its time it stayed in suspended mode and will compensate for it (or ask the patient if he wants any compensation) by increasing its infusion rate when leaving the suspended mode. This compensation may be partial or total. It may be done rapidly or over a predefined period of time. If done over a predefined period of time, it may be constant or follow a specific profile.

In one embodiment, the system is designed in such a manner as to detect an infusion anomaly condition and allow for its compensation after its release including the following steps:

detecting an infusion anomaly condition entering into a safe state mode where the pump stops infusing checking if the above condition is still present when such condition is released, exiting the safe state and resume infusion calculating the missed amount of fluid that was supposed to be infused during the time where the infusion pump was in safe state determining the compensation amount that will be infused as compensation of the missed amount infusing the compensation amount The step of checking the presence of the infusion anomaly condition may be regularly repeated until such condition is released. This step may be performed after a predetermined time or at different time. The determination of the compensation amount may be done by applying a predetermined correction factor to the missed amount. This predetermined factor may be constant for a given drug, it may also vary according to known or measured parameters. In one possible embodiment, this factor may be adapted in function of the time spent in safe state. The compensation amount may be infused over a predefined period of time. It may require user acknowledgement before infusion.

In some cases, the system may inform the patient if the compensation amount reaches a predefined threshold. The compensation amount may be possible after a validation of the patient. In other case, when the event is removed, before to infuse a compensation amount, the medical system may prompt the patient to check his blood glucose level. Thus, the compensation amount may take into account the current blood glucose level and the event (in particular the non-delivered amount of drug during the event)

In other cases, the suspended mode may be automatically enabled (by the processor) when the pump is disconnected (from its patch, as described above). For, example, the hall effect sensor may send a signal to the processor and then the pumping device stops the infusion and switches in a suspended mode.

Figure 16:
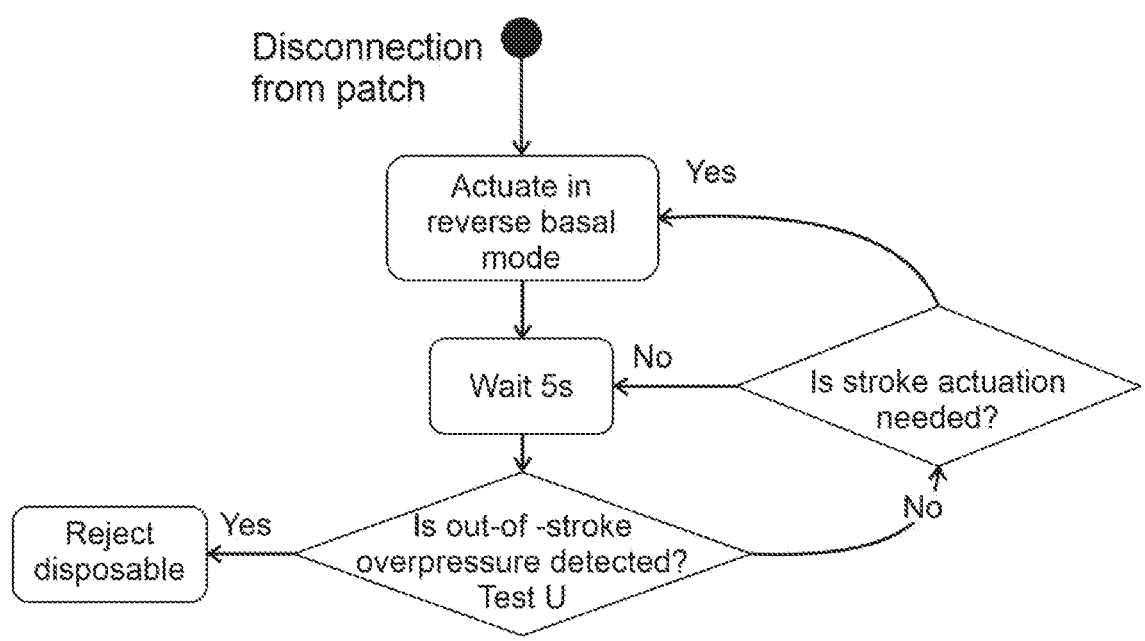
FIG. 16 shows the sequence when the pumping device is disconnected form the patch or when the pumping device is in suspended mode.

Nevertheless when the pumping device is in a suspended mode in order to avoid insulin drying in the fluidic pathway, the processor may command a low basal rate. The workflow of this operating mode is described in the FIG. 16.

Other Operating Modes

An indication device (as disclosed above) has to alert the patient when an event or fault condition that could prevent accurate drug infusion is detected. But sometimes the sensor may detect an event which is similar to a fault condition and is not a real fault condition. The processor has to interpret in a clever way the data in such a manner to alert or inform the patient only when necessary.

Figure 5:
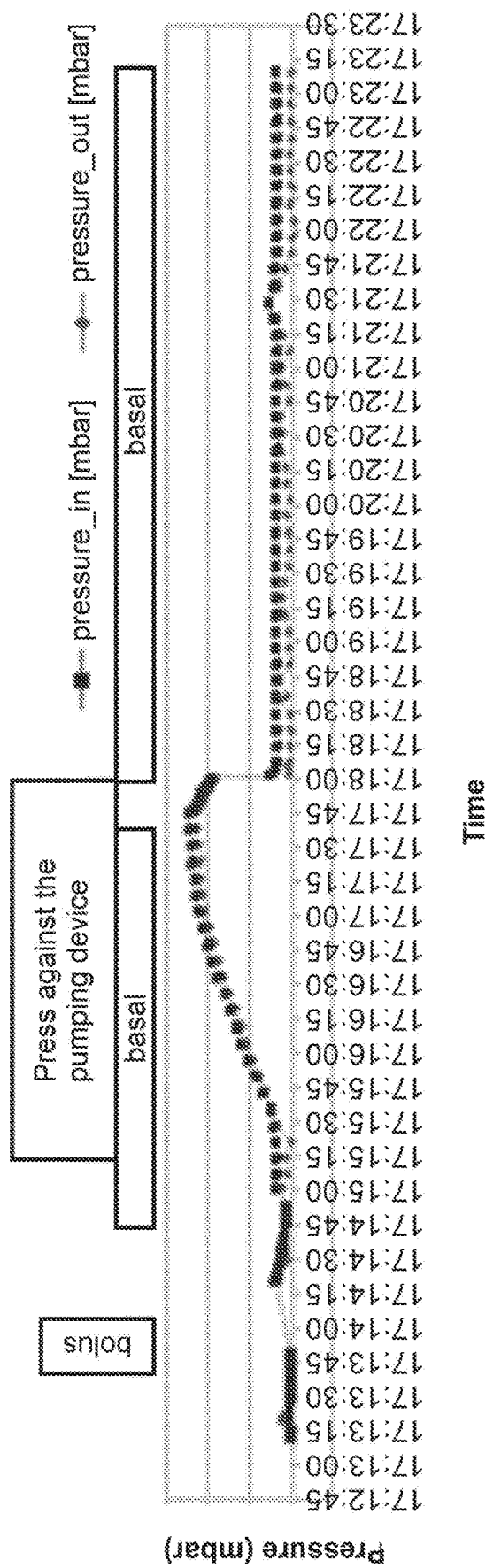
FIG. 5 shows the pressure measured by two pressure sensors when the pumping device infuses a fluid to the patient and when the patient presses against the pumping device or infusion set.

For example, when the patient moves, the sensor can detect abnormal pressure but the processor does not trigger the alarm. The FIG. 5 shows a pressure data of a first and second pressure sensor when the patient presses against the pumping unit and/or the infusion site. For example: the occlusion may be caused by the patient if the patient sleeps on the pumping unit or infusion site or when he contracts the muscle in which or against which the cannula injects the fluid. The pressure of both sensors increases and reaches a very high pressure, but the processor does not trigger the alarm and may switch temporary in suspended mode. Thus even if the pressure reaches a pressure which can be bigger than some thresholds, the processor does not immediately trigger the alarm. If the pressure is maintained for too long, the processor can indicate to the patient that he shall move in such a way to stop pressing against the infusion site or pumping unit. Other events, such as physical activity (muscle contraction), cannula removal and the like, may also be detected by the processor and help render a better interpretation of the alarm condition.

In one embodiment, the system is designed in such a manner as to detect an infusion anomaly condition and to allow for its compensation after its release, including the following steps:
- detecting an infusion anomaly condition
- waiting a predetermined time
- after said predetermined time checking if the above condition is still present
- If the above condition is still present, informing the patient
- If the above condition is not present any more, resume the infusion Said infusion anomaly condition may be for example a disconnection of the pump from the infusion set or patch, an occlusion, an increasing of the fluidic restriction in the fluidic pathway (due to a muscle contraction, a mechanical pressure on the infusion site or set).

If an infusion anomaly condition is detected (for example a partial occlusion occurs), the alarm may be triggered only when there is a risk of under infusion that could put the patient at risk or only in a case of an imminent health hazard. The estimation of the potential under infusion depends on the level of pressure reached at the end of the actuation. Since the pressure release is slow, the effect of partial occlusion is usually more problematic in bolus mode or in fast basal mode. Thus, the system may control the actuator in such a way as to limit the effect of the partial occlusion. For example, the processor may decrease the speed of the stroke (for example during a push action) or may maintain during a predetermined time the actuator in full push position so as to force the fluid to flow through the (partial) occlusion or the actuation (of the pump) may be temporarily stopped so as to wait that the fluid is actually at least partially injected in the infusion site. In this case, the infusion time is longer but the patient receives the right amount of fluid as programmed for his therapy. A high pressure in the patient line prevents the correct closure of the outlet valve. The minimum pressure necessary to prevent this outlet valve close is a function of the outlet valve design, in particular its opening threshold. Once the pressure in the patient line, after actuation, decreases below said minimum pressure, the triggering of a pull movement will not induce backflow through the outlet which can prevent pumping accuracy.

In one embodiment, the system is adapted to perform some or all of the following steps when a partial occlusion is detected:
- Detecting an partial occlusion
- Reducing the speed of the actuator during the push phase, and/or
- Maintaining at least temporarily the actuator at the full push position, and/or
- Applying a pause between two strokes during a predetermined time, said predetermined time depending of the fluidic resistance.

Preferentially, once a partial occlusion is detected, the actuation profile may be modified by increasing the push hold time by a additional duration $T_{ph}$ (said additional duration being introduce the next actuation following the occlusion detection) in order to infuse the full stroke volume to the patient.

Thus the new push hold time depends on $P_{Din}$ and to determine the push hold time $T_{ph}$, two options are then proposed:
1—$P_{Din}$ is measured and analyzed in real time during actuation and the pull movement of the piezo is triggered by $P_{Dint} < P_{occp}$.
2—$P_{Din}$ is analyzed after actuation and if $P_{Din}$>predetermined value (for example $P_{occp}$), the next stroke will be performed with a larger push hold time. The new push hold time can be calculated as a function of the level of the restriction occurring at the outlet of the pump. The extra delay to add to $T_{ph}$ at the next stroke to ensure the pressure at the end the push is lower than $P_{occp}$ can be calculated as:

$$T_{ph} = \Delta t \cdot \frac{\ln\left(\frac{P_{occp}}{P_{i3}}\right)}{\ln\left(\frac{P_{i3}}{P_{i2}}\right)}$$

Where $\Delta t$ is the delay between the measurement of $P_{i3}$ and $P_{i2}$ (for example $\Delta t$=0.2 s).

Note: after a stroke, the outlet valve remains open as long as the $P_{Dint} > P_{occp}$. Therefore the outer detector is submitted to the same pressure if this latter condition is fulfilled, and thus the outer detector could also be used for partial occlusion management.

In other case, once a partial occlusion is detected, the actuation profile may be modified by increasing the push hold time $T_{ph}$ (of at least one future actuation) in order to infuse the full stroke volume to the patient. Thus the new push hold time depends on $P_{out}$ and to determine the push hold time $T_{ph}$, two options are then proposed:
1—$P_{out}$ is measured and analyzed in real time during actuation and the pull movement of the piezo is triggered by $P_{out} < P_{occp}$.

2—$P_{out}$ is analyzed after actuation and if $P_{out}$>predetermined value (for example $P_{occp}$), the next stroke will be performed with a larger push hold time. The new push hold time can be calculated as a function of the level of the restriction occurring at the outlet of the pump. The extra delay to add to $T_{ph}$ at the next stroke to ensure the pressure at the end the push is lower than $P_{occp}$ can be calculated as:

$$\Delta t' = \Delta t \cdot \frac{\ln\left(\frac{P_{out_1}}{P_{occp}}\right)}{\ln\left(\frac{P_{out_0}}{P_{out\_1}}\right)}$$

Where $\Delta t$ is the delay between the measurement of $P_{out\_1}$ and $P_{out\_2}$ (for example $\Delta t=0.2$ s).

If the infusion anomaly condition occurs several times but is removed after each predetermined time, the system may inform the patient once the fault tolerance time for said failure mode is reached.

The principle of detection as disclosed above may be possible with other sensors such as flow sensor, proximity sensor, accelerometer or alternate sensors located in the pumping chamber or in the system.

Displaying Relevant Information

Status of the Infusion Set

The system may be designed to evaluate the status of the infusion site. Indeed, the infusion site and/or the cannula may change over time. For example, the permeability of the cannula may change, a nodule may develop near the infusion site or an inflammation near the infusion site may occur.... Thus, it will be useful for the patient to know over time this evolution.

In one embodiment, the infusion system (the medical system) comprises a pumping device, a processor and an indication device. The processor may be adapted to anticipate the evolution over time. Thus, the processor may comprise a mathematical model which estimates when the infusion site or cannula has to be changed. Preferentially, the system further comprises a sensor which is used by the processor and the mathematical model. Said sensor may be a pressure sensor. The sensor and the processor are adapted to assess the status of the infusion set (or the characteristic of the infusion site), and the indication device is adapted to inform the patient about this status. The processor may take account the "normal" life cycle of the infusion set.

Figure 6:
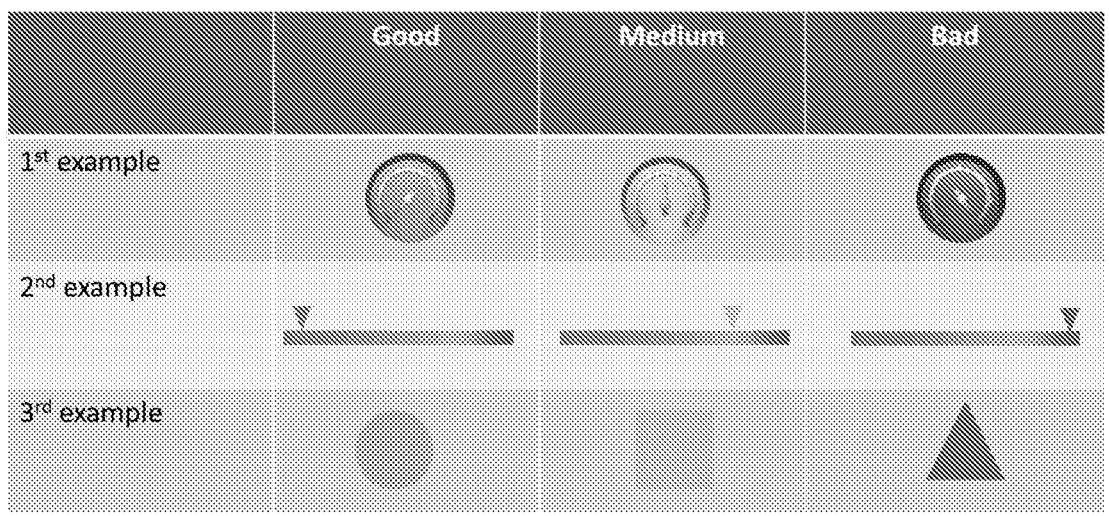
FIG. 6 shows few examples of indication devices which illustrate three distinct status of an element of the system.
Figure 7:
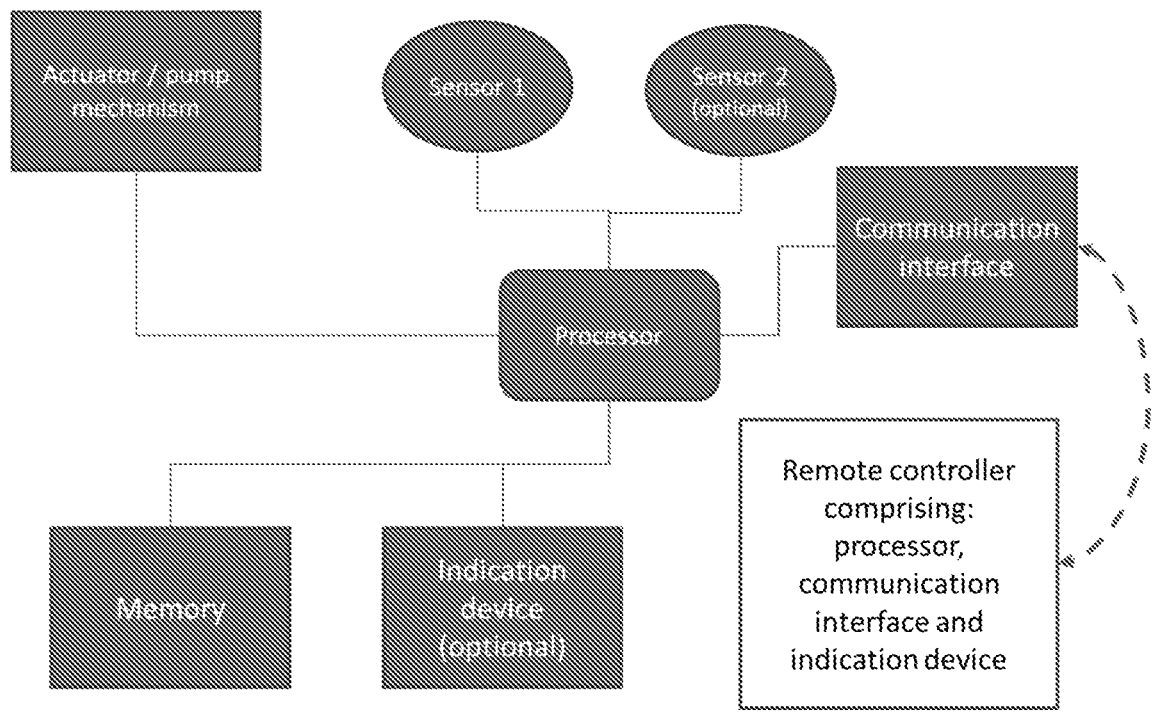
FIG. 7 illustrates a pumping device comprising some potential features.
Figure 8:
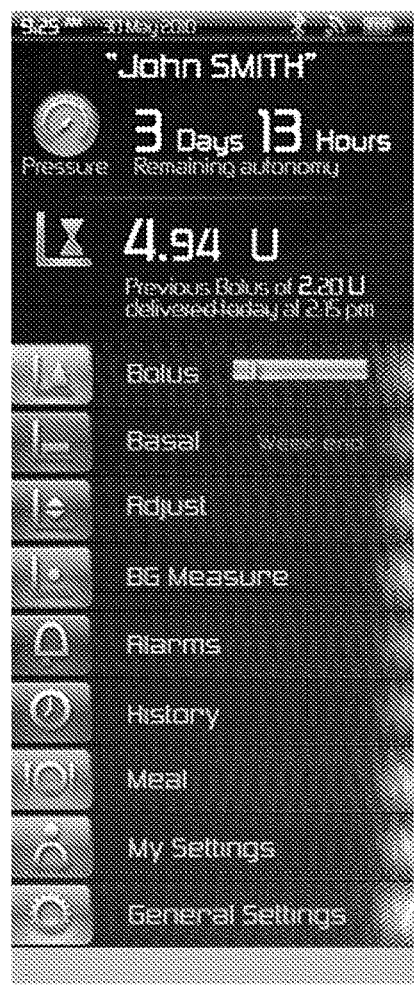
FIG. 8 shows an example of a display with an indication device.

As disclosed by the FIG. 6, the indication device may display an indicia which may be an icon or a bar chart (with specific shapes or colors). The screen of the remote controller (FIG. 1e) displays such indicia. Said indication device quickly and easily informs the patient of the infusion site status or cannula status in terms of functionality and/or diffusion of the drug. Said indication device may appear on a screen of the system (on the pumping device or on a remote control which is a distinct device of the pumping device) and may be displayed at a specific area of the screen. In particular, the FIG. 8 shows a screen of the medical system. Said screen may comprise successive displays which are changed automatically or by an action of the user. The screen comprises a home page in which a specific area is dedicated to display the status of the infusion set or the characteristic of the infusion site or other information described in this document. The home page may concurrently display the status of the infusion set and a status of the medical device (operating mode, current or previous bolus infusion, current basal infusion, reservoir level, ... ) or several menus (icons of bolus, basal, adjust, alarms, history, BG Measure) or the last measurement of blood glucose level of the patient. Furthermore, the processor may estimate the remaining autonomy (life cycle) of the infusion set. This indication device may further display the amount of drug which is non-infused and the operating mode of the pump (suspended mode, normal mode, ... ).

Characteristics of the Infusion Site

The indication device may further show a flow rate and/or a real amount infused and/or an interstitial pressure and a display may draw a profile or a direction arrow (up or down) of this information so that the patient can see a trend of the status of the infusion site. Said system may assess the infusion site so as to inform the patient if the location of the infusion site is good or not and may prompt to change its location. It's very important for the patients which are too light-weight, because the infusion is more difficult for these patients and the system may trigger occlusion alerts due to the location. Thus, after a test of the system, the system can advise the patient about the choice of the infusion site location.

Advices Displayed by the Medical System

As described above, the indication device may be adapted to inform the patient or a caregiver in a manner as to prompt to:

Change the infusion site (a new cannula, location of the cannula, ... ),

Adopt a behavior (massage of, press against or pull the infusion site ... ).

In one embodiment, the system is adapted to perform the following steps when an infusion anomaly is detected:

Detecting a condition of partial or total occlusion or a condition of infusion limitation or restriction in the infusion line, Prompting the patient to (at least one action of the following list):

change all or part of the infusion line or change the infusion site (the location where the cannula injects the fluid)

In one embodiment, the system is adapted to perform the following steps when a potential infusion anomaly is detected:

Detecting a condition of infusion limitation or restriction in the infusion line, Computing the fluidic resistance in the infusion line, Informing the user about:

The flow rate which may be reached at the specific infusion site, and/or

The absorption capability of the specific infusion site, and/or

The status of the infusion site, and/or

The status of the cannula, and/or

An opinion on the cannula location.

Thus, instead of changing the cannula, the system may be designed to prompt the user to massage the infusion site. In one embodiment, the system comprises an indication device which may be a led, a screen, a sound or a vibration. Said indication device is adapted to inform the patient about the anomaly and/or prompt a specific behavior. In some cases, if the occlusion is limited, the indication device can display just the information or the advice and when the occlusion is important, the indication device alerts and asks, requests, encourages or requires a specific behavior.

In embodiment, the system is adapted to perform the following steps when an occlusion is detected:

Detecting an occlusion by the processor,

Prompting a specific behavior so as to release the occlusion,

Optionally, displaying on an indication device the cause of the infusion anomaly.

Figure 9:
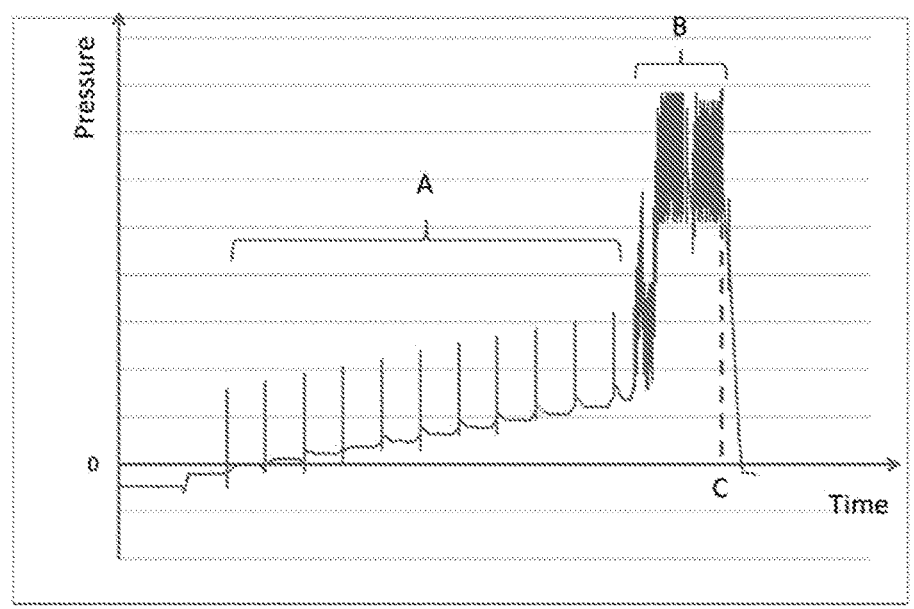
FIG. 9 shows a pressure profile where the infusion site is occluded and then released.
Figure 10:
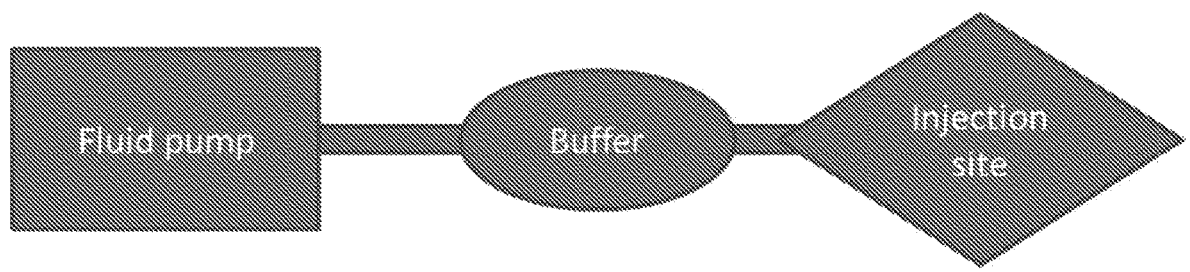
FIG. 10 shows an embodiment with a buffer.

The FIG. 9 discloses a pressure profile which may occur when the infusion site is occluded or when a mechanical stress is applied on the infusion site. During a first part (called A), the pump is actuated with several strokes with basal stroke. The pressure sensor records a small increase of the pressure at each stroke. The processor can monitor the trend of the fluid pressure or the mobile average of the received signal (for example Pi2 of each stroke) so as to detect the anomaly infusion. During the second part (called B), the pump is actuated with bolus stroke. A basal stroke may be integrated between two bolus strokes. The bolus stroke is characterized by an important infusion rate and in case of occlusion the fluid pressure is increasing rapidly. Once the occlusion detected, the medical device may prompt the user to massage the infusion site. At the point C, the user massages the infusion site and the pressure comes back at normal data. In other terms, the release of an occlusion or a mechanical stress on the infusion set can occur when the infusion site is moved or massaged by a user.

In another embodiment, the system may comprise means arranged to have the same effect (of a specific behavior asked as disclosed above), for example said means may be adapted to move the cannula in such a manner as to release the occlusion or the mechanical constrains. The cannula may comprise a piezoelectric element which moves or vibrates when the processor actuates this element.

In one embodiment, the system is adapted to perform the following method when an occlusion is detected, said method comprising the following steps:

Detecting an occlusion by the processor,

Actuating the means for releasing the occlusion.

Thus, the system can monitor the infusion line in particular the cannula in such a way to prompt a specific action. The processor may also monitor the trend of the pressure and detects an increase of the fluidic resistance. Thanks to this trend, the system can prevent in advance the establishment of an occlusion or the aging of the cannula. Said indication device may be also used to display the status of the infusion site, a percentage of restriction in the infusion line, the permeability level of the cannula.

In this case, the processor may command another additional stroke to release the occlusion. Said additional stroke may be a standard or reverse basal or bolus stroke and the processor may take into account the delivered amount of fluid by this stroke. The medical system may inform the patient about the additional delivery and the processor may check that the additional delivery is not unsafe for the patient.

The invention claimed is:

1. A fluid delivery system for delivering a fluid to a patient comprising:
    a reservoir;
    an infusion set;
    a fluidic pathway configured to provide a fluid communication from the reservoir to the infusion set;
    a pumping unit configured to move the fluid through the fluidic pathway;
    a sensor; and
    a processor configured to control the pumping unit, receive a signal from the sensor, detect an occurrence of an infusion anomaly based on the received signal of the sensor, estimate an amount of undelivered fluid as a result of an underdelivery by the fluid delivery system based on an amount of undelivered strokes by the pumping unit, and determine a compensation amount to be infused as compensation for the undelivered fluid, wherein the compensation amount takes into account a blood glucose level of the patient.

2. The system according to the claim 1 further comprising: a counter configured to store an estimation of the amount of the undelivered strokes of the pumping unit.

3. The system according to the claim 1, wherein the signal of the sensor comprise data that relates to a fluid pressure in the fluid pathway.

4. The system according to the claim 1, wherein the infusion anomaly is an occlusion.

5. The system according to the claim 4, wherein once the occlusion is detected, the processor is configured to maintain the pumping unit in a push position during a time period.

6. The system according to the claim 5, wherein the time period is predetermined or determined according to the signal generated by the sensor.

7. The system according to the claim 1, wherein once the infusion anomaly is released, the processor is configured to infuse at least a part of the amount of the undelivered fluid.

8. The system according to the claim 1, wherein the compensation amount takes into account an estimation of the undelivered fluid.

9. The system according to the claim 1, wherein the processor is further configured to control the pumping unit according to a first actuation profile and a second actuation profile which is different form the first actuation profile.

10. The system according to the claim 9, wherein the first actuation profile comprises a two partial pull actuations separated by a full push actuation and the second actuation profile comprises a two partial push actuations separated by a full pull actuation.

11. The system according to the claim 1, wherein the processor is configured to determine a status of the infusion set and/or a characteristic of the infusion site.

12. The system according to the claim 11 further comprising:
    an indication device configured to inform a user about the status of the infusion set and/or the characteristic of the infusion site.

13. The system according to the claim 12, wherein the indication device displays an information corresponding to a quality of the infusion set, and/or the characteristic of the infusion site and/or a fluidic resistance at the infusion site and/or a remaining time before a change of the infusion set.

14. The system according to the claim 12, wherein the indication device is configured to display a color index depending on the status of the infusion set.

15. The system according to the claim 1, wherein once the infusion anomaly is detected, the processor is configured to trigger an alarm.

16. The system according to the claim 1, wherein the processor is configured to switch from a normal operating mode to a suspended operating mode in which the pumping unit is stopped leading to the underdelivery of the fluid.

17. The system according to the claim 16, wherein the processor is configured to estimate an amount the underdelivery of the fluid due to the suspended operating mode.

18. The system according to the claim 16, wherein during the suspended operating mode, the processor is configured to actuate the pump unit in order to prevent fluid drying in the fluidic pathway.

19. The system according to the claim 1, wherein the sensor is configured to measure a pressure in the fluidic pathway and/or a pressure in a pumping chamber of the pumping unit.

20. A fluid delivery system for fluid delivery to a patient comprising:
- a reservoir;
- an infusion set;
- a fluidic pathway configured to provide a fluid communication from the reservoir to the infusion set;
- a pumping unit configured to move the fluid through the fluidic pathway;
- a sensor; and
- a processor configured to control the pumping unit, receive a signal from the sensor, detect an occurrence of an infusion anomaly based on the received signal of the sensor, estimate an amount of undelivered fluid as a result of an underdelivery by the fluid delivery system, and switch from a normal operating mode to a suspended operating mode where the fluid delivery is stopped leading to the underdelivery of the fluid, and
- wherein during the suspended operating mode, the processor is configured to actuate the pumping unit to prevent fluid drying in the fluidic pathway.

* * * * *

UNITED STATES PATENT AND TRADEMARK OFFICE
CERTIFICATE OF CORRECTION

Page 1 of 1

PATENT NO. : 10,668,212 B2
APPLICATION NO. : 15/505936
DATED : June 2, 2020
INVENTOR(S) : Frédéric Neftel, Christophe Conan and Eric Chappel It is certified that error appears in the above-identified patent and that said Letters Patent is hereby corrected as shown below:

On the Title Page

Left column, Lines 3-4:
(72) Inventors should read:
Frédéric Neftel, Crans-Montana (CH);
Christophe Conan, Lausanne (CH);
Eric Chappel, Lausanne (CH).

Signed and Sealed this
Sixth Day of October, 2020

Andrei Iancu
*Director of the United States Patent and Trademark Office*